US008925784B2

(12) United States Patent
Marczyk et al.

(10) Patent No.: US 8,925,784 B2
(45) Date of Patent: Jan. 6, 2015

(54) SURGICAL FASTENER-APPLYING APPARATUSES WITH SEQUENTIAL FIRING

(71) Applicant: Covidien LP, Mansfield, MA (US)

(72) Inventors: Stanislaw Marczyk, Stratford, CT (US); Dino Kasvikis, Mansfield, MA (US); Kevin Sniffin, Danbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/965,802

(22) Filed: Aug. 13, 2013

(65) Prior Publication Data

US 2014/0021241 A1   Jan. 23, 2014

Related U.S. Application Data

(62) Division of application No. 12/983,907, filed on Jan. 4, 2011, now Pat. No. 8,517,242.

(51) Int. Cl.
*A61B 17/072* (2006.01)
*A61B 17/068* (2006.01)

(52) U.S. Cl.
CPC ........ *A61B 17/07207* (2013.01); *A61B 17/072* (2013.01); *A61B 17/068* (2013.01); *A61B 2017/07278* (2013.01)
USPC .................. 227/176.1; 227/175.1; 227/178.1; 227/19

(58) Field of Classification Search
CPC .............. A61B 17/068; A61B 17/072; A61B 17/07207; A61B 17/07278
USPC ............................ 227/175.1, 176.1, 178.1, 19
See application file for complete search history.

(56) References Cited

U.S. PATENT DOCUMENTS

| | | | |
|---|---|---|---|
| 4,665,916 A | 5/1987 | Green | |
| 5,415,334 A | 5/1995 | Williamson et al. | |
| 5,816,471 A | 10/1998 | Plyley et al. | |
| 5,964,394 A | 10/1999 | Robertson | |
| 6,786,382 B1 | 9/2004 | Hoffman | |
| 6,988,650 B2 | 1/2006 | Schwemberger et al. | |
| 7,070,083 B2 | 7/2006 | Jankowski | |
| 7,275,674 B2 | 10/2007 | Racenet et al. | |
| 7,398,908 B2 | 7/2008 | Holsten et al. | |
| 7,401,721 B2 | 7/2008 | Holsten et al. | |
| 7,407,075 B2 | 8/2008 | Holsten et al. | |
| 7,407,076 B2 | 8/2008 | Racenet et al. | |
| 7,431,730 B2 | 10/2008 | Viola | |
| 7,455,676 B2 | 11/2008 | Holsten et al. | |
| 7,455,682 B2 | 11/2008 | Viola | |
| 7,461,767 B2 | 12/2008 | Viola et al. | |
| 7,464,847 B2 | 12/2008 | Viola et al. | |
| 7,472,816 B2 | 1/2009 | Holsten et al. | |
| 7,481,349 B2 | 1/2009 | Holsten et al. | |
| 7,517,356 B2 | 4/2009 | Heinrich | |
| 7,588,174 B2 | 9/2009 | Holsten et al. | |

(Continued)

*Primary Examiner* — Michelle Lopez

(57) ABSTRACT

A surgical fastening instrument is provided. The surgical fastening instrument includes a handle portion and an elongate portion extending distally from the handle portion and defining a longitudinal axis along a length thereof. The surgical fastening instrument also includes an end effector assembly that includes an anvil and a cartridge supported adjacent a distal end of the elongate portion. Each of the anvil and the cartridge includes a tissue contacting surface oriented substantially perpendicular to the longitudinal axis. One or more independently movable pushers is configured to support one or more surgical fasteners. A thrust bar is operatively coupled to the elongate portion, wherein the thrust bar is movable over a predetermined stroke to effect sequential ejection of at least two surgical fasteners of the plurality of surgical fasteners from the cartridge.

4 Claims, 26 Drawing Sheets

(56) References Cited

U.S. PATENT DOCUMENTS

| | | | |
|---|---|---|---|
| 7,635,073 B2 | 12/2009 | Heinrich | |
| 7,641,092 B2 | 1/2010 | Kruszynski et al. | |
| 7,648,055 B2 | 1/2010 | Marczyk | |
| 7,699,204 B2 | 4/2010 | Viola | |
| 7,708,182 B2 | 5/2010 | Viola | |
| 7,717,312 B2 | 5/2010 | Beetel | |
| 7,717,313 B2 | 5/2010 | Criscuolo et al. | |
| 7,726,538 B2 | 6/2010 | Holsten et al. | |
| 7,726,539 B2 | 6/2010 | Holsten et al. | |
| 7,744,624 B2 | 6/2010 | Bettuchi | |
| 7,744,628 B2 | 6/2010 | Viola | |
| 7,748,097 B1 | 7/2010 | Matthews et al. | |
| 7,757,925 B2 | 7/2010 | Viola et al. | |
| 7,766,207 B2 | 8/2010 | Mather et al. | |
| 7,823,760 B2 | 11/2010 | Zemlok et al. | |
| 7,828,188 B2 | 11/2010 | Jankowski | |
| 7,828,189 B2 | 11/2010 | Holsten et al. | |
| 7,837,079 B2 | 11/2010 | Holsten et al. | |
| 7,837,081 B2 | 11/2010 | Holsten et al. | |
| 7,845,534 B2 | 12/2010 | Viola et al. | |

FIG. 6A  FIG. 6A-1

SURGICAL FASTENER-APPLYING APPARATUSES WITH SEQUENTIAL FIRING

CROSS-REFERENCE TO RELATED APPLICATIONS

This application is a divisional claiming the benefit of and priority to U.S. patent application Ser. No. 12/983,907, filed Jan. 4, 2011, now U.S. Pat. No. 8,517,242 and the entire disclosure of which the above-identified application is hereby incorporated by reference herein.

BACKGROUND

1. Technical Field

The present disclosure relates generally to surgical fastener-applying apparatuses and, more specifically, to surgical fastener-applying apparatuses that employ sequential firing.

2. Background of Related Art

Surgical fastener-applying apparatuses used for applying a plurality of fasteners (e.g., surgical staples) through compressed living tissue are well known in the art. These surgical fastener-applying apparatuses are commonly employed for closing tissue or organs prior to transaction or resection, for occluding organs in thoracic and abdominal procedures, and for fastening tissue in anastomoses.

Typically, such surgical fastener-applying apparatuses include an end effector assembly, which includes an anvil assembly and a cartridge assembly for supporting a plurality of surgical fasteners, an approximation mechanism for approximating the anvil and cartridge assemblies, and a firing mechanism for ejecting the surgical fasteners from the cartridge assembly.

In certain types of surgical instruments, such as traverse anastomoses stapling instruments, the surgical fasteners are typically configured to deploy simultaneously from the cartridge from which they are supported. Since the surgical fasteners are fired and deployed simultaneously, a significant amount of force is required by a user to effectively operate a handle of the surgical fastener-applying apparatus.

SUMMARY

The present disclosure relates to a surgical stapling instrument. The surgical fastening instrument includes a handle portion and an elongate portion extending distally from the handle portion and defining a longitudinal axis along a length thereof. The surgical fastening instrument also includes an end effector assembly that includes an anvil and a cartridge supported adjacent a distal end of the elongate portion. Each of the anvil and the cartridge includes a tissue contacting surface oriented substantially perpendicular to the longitudinal axis. One or more independently movable pushers are configured to support one or more surgical fasteners. A thrust bar is operatively coupled to the elongate portion, wherein the thrust bar is movable over a predetermined stroke to effect sequential ejection of the plurality of surgical fasteners from the cartridge.

The present disclosure also relates to an end effector assembly adapted for use with a surgical stapling instrument. The end effector includes an anvil assembly and a cartridge assembly. A plurality of independently movable pushers is configured to support a plurality of surgical fasteners. Each of the anvil assembly and cartridge assembly includes a tissue contacting surface that is oriented substantially perpendicular to a longitudinal axis of an elongate portion of the surgical stapling instrument. A camming member is disposed in mechanical cooperation with the cartridge assembly, wherein the camming member is configured to engage a portion of the surgical stapling instrument to effect sequential firing of the surgical staples from the cartridge assembly.

The present disclosure also relates to a method of surgically joining tissue via sequentially ejecting surgical fasteners using a surgical fastening instrument.

BRIEF DESCRIPTION OF FIGURES

Various embodiments of the presently disclosed surgical fastening instrument are disclosed herein with reference to the drawings, wherein.

Figure 6B:
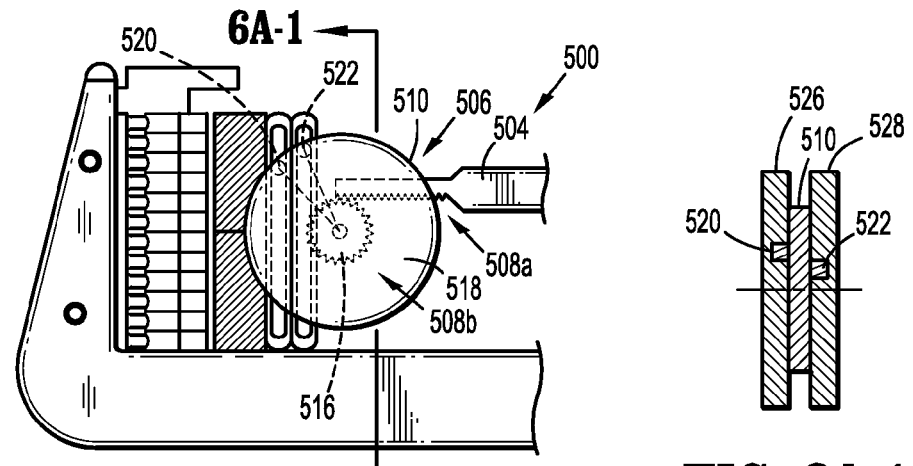
FIGS. 6A-6C are cut-away side views of a firing mechanism that includes a camming configuration in accordance with another embodiment of the present disclosure.
Figure 6B:
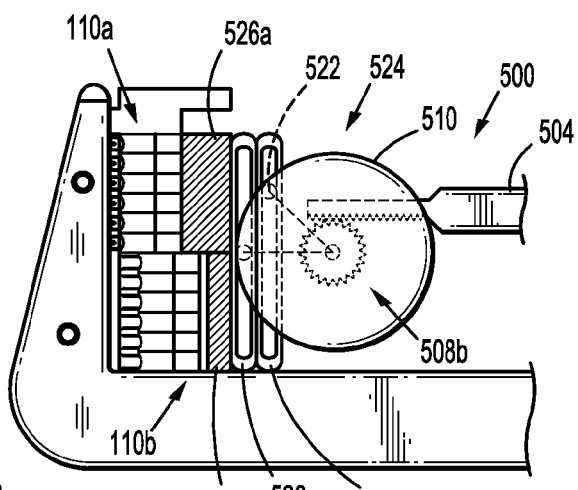
Figure 6C:
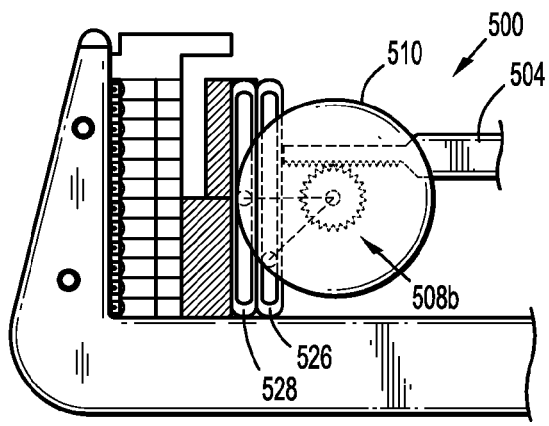
Figure 6D:
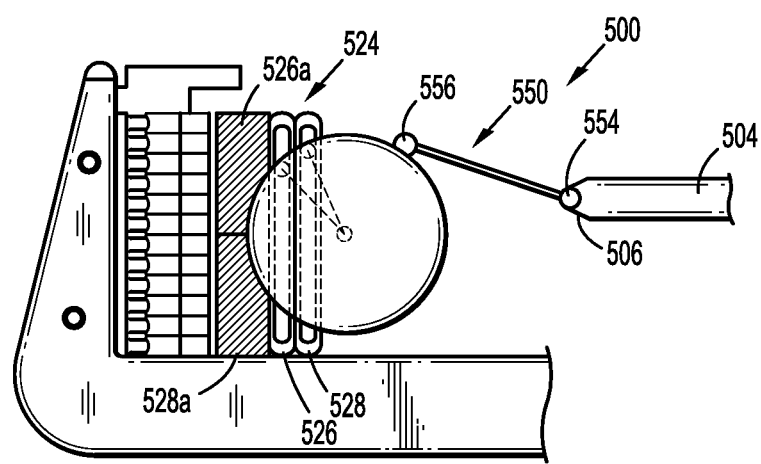
Figure 7A:
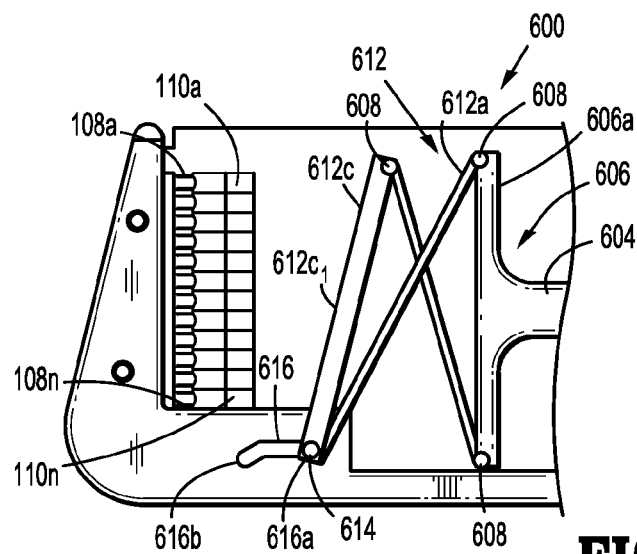
Figure 7B:
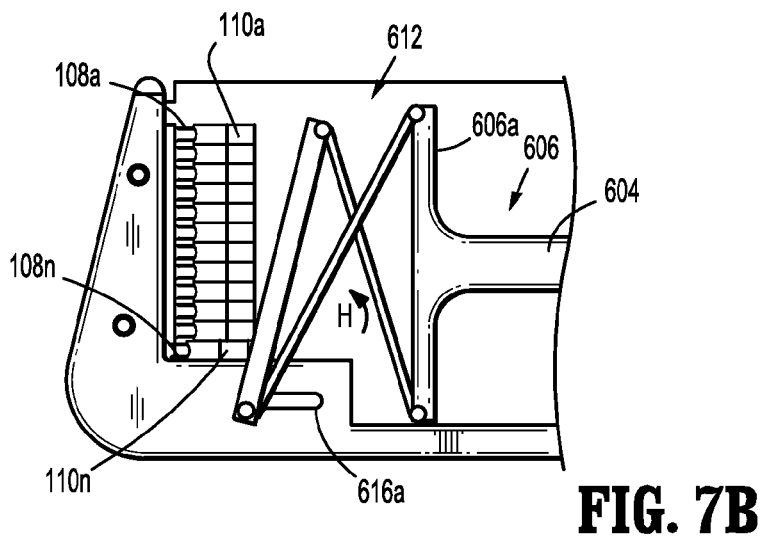
Figure 7C:
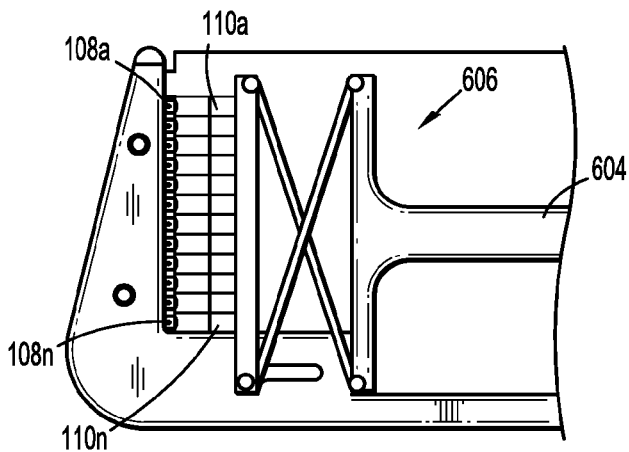
Figure 7D:
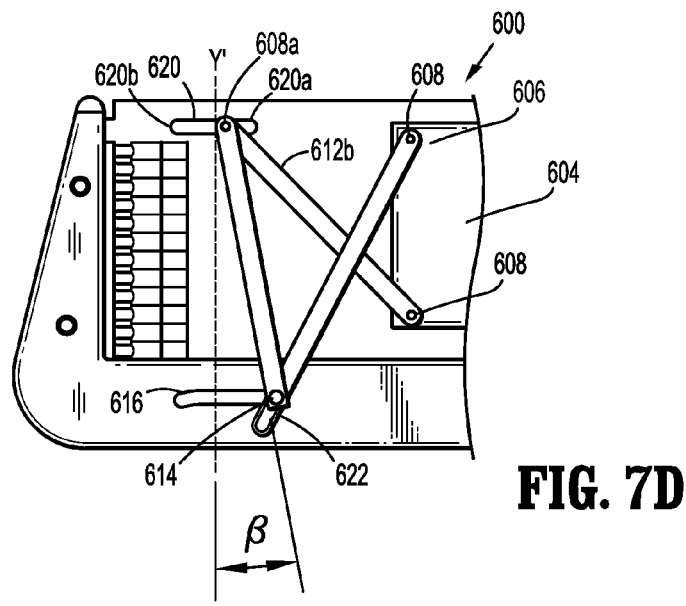
Figure 7E:
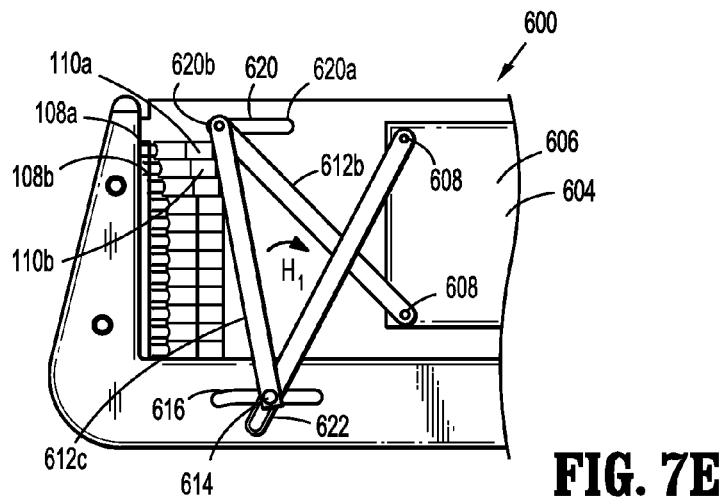
Figure 7F:
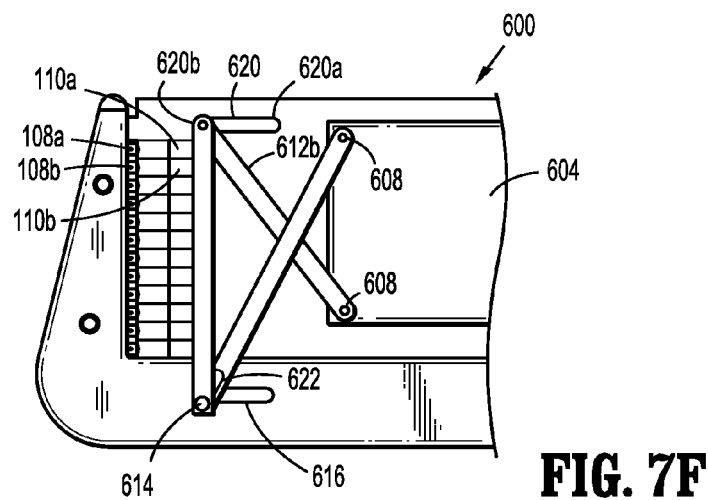
Figure 8A:
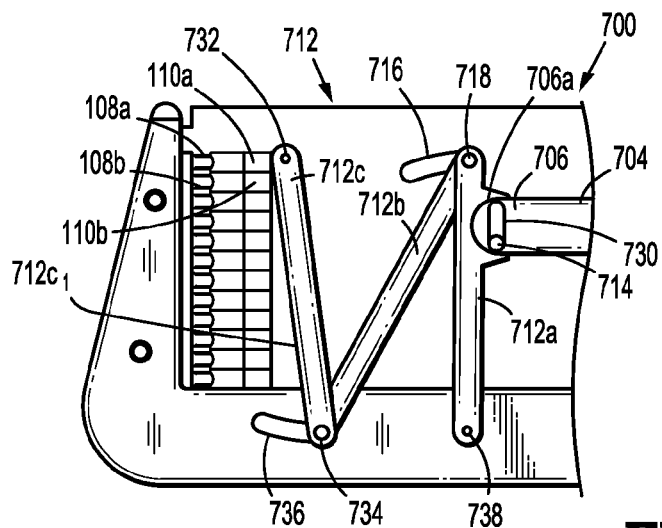
Figure 8B:
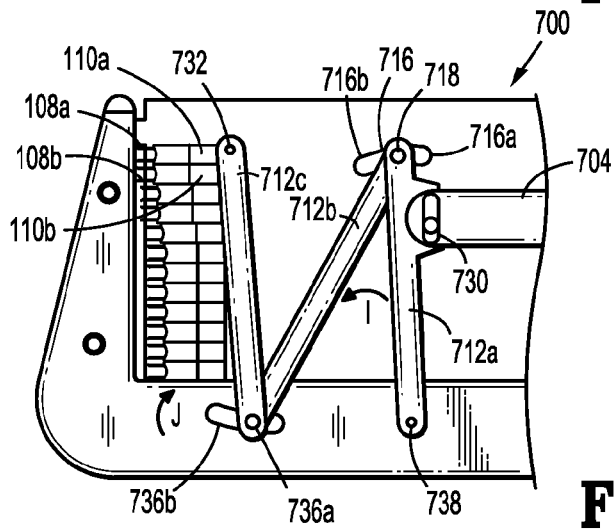
Figure 8C:
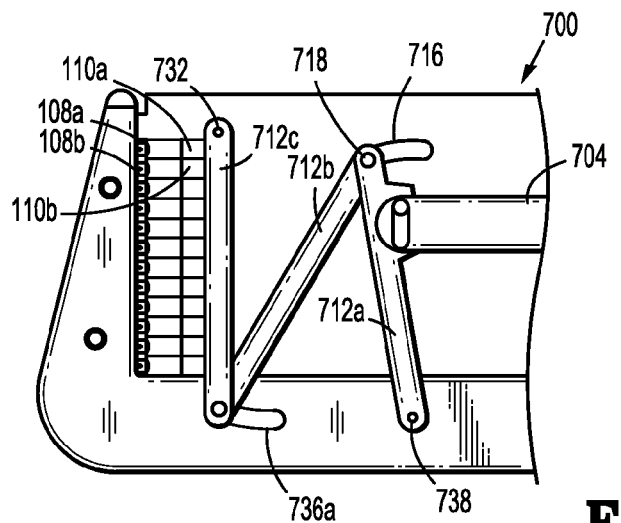
Figure 8D:
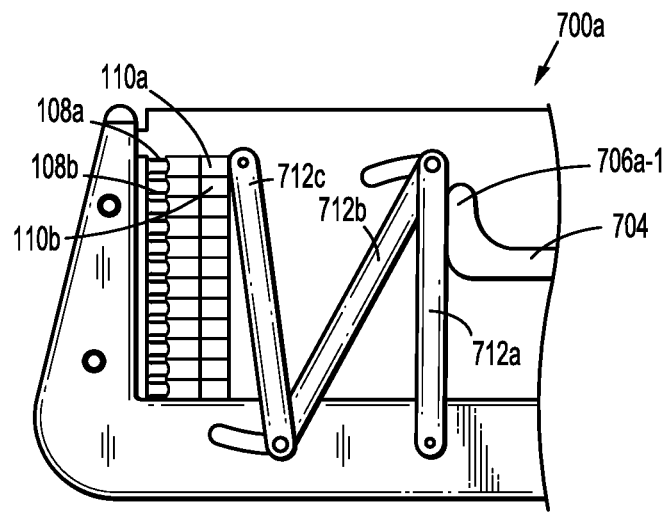
Figure 8E:
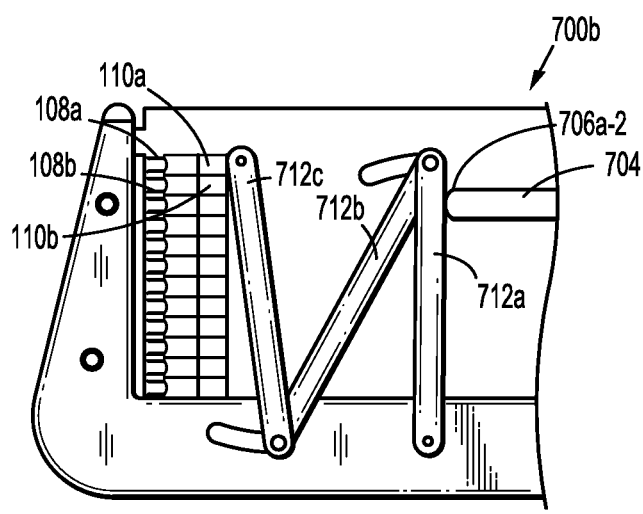
Figure 9A:
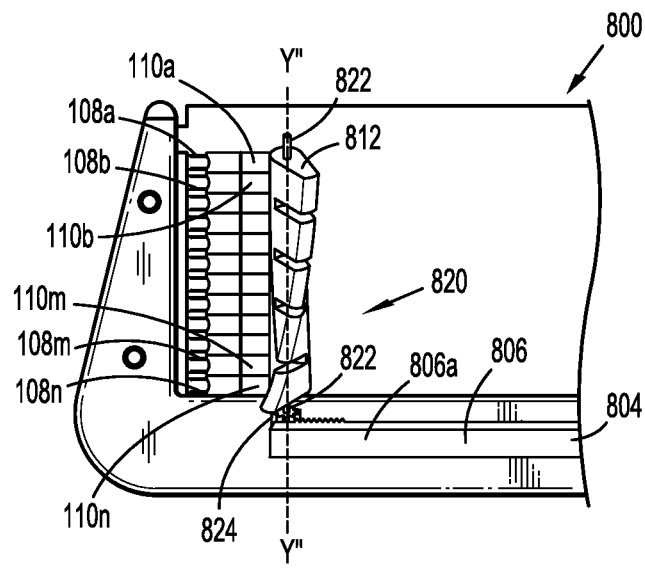
Figure 9B:
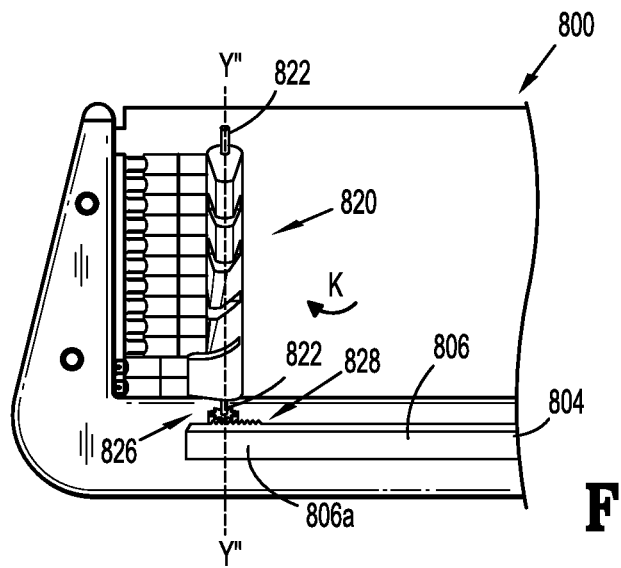
Figure 9C:
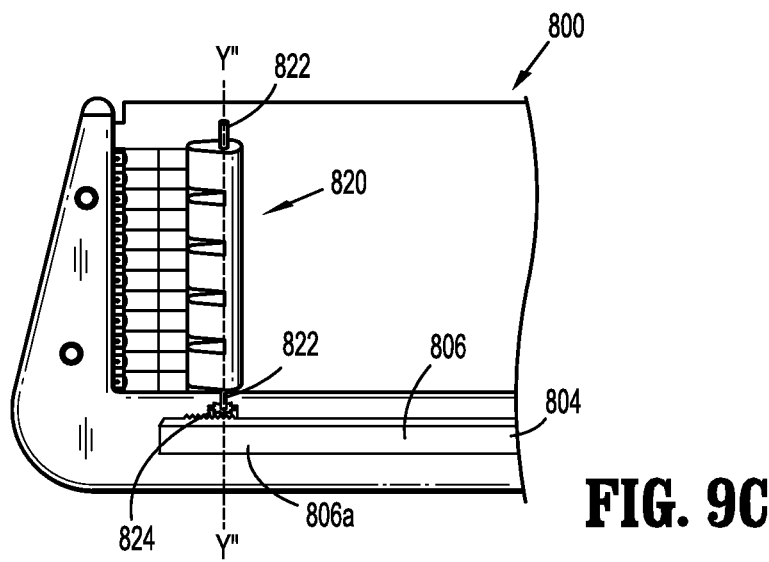
Figure 9D:
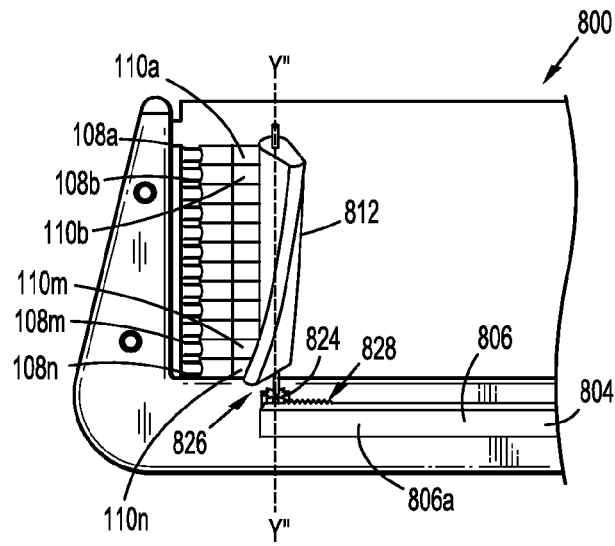
Figure 9E:
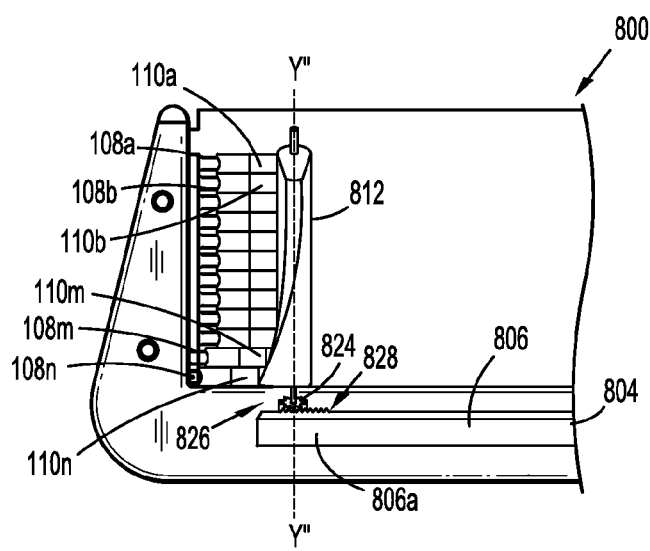
Figure 9F:
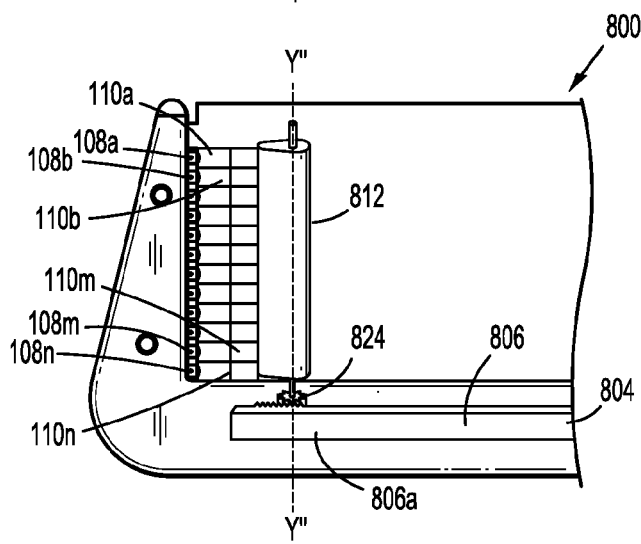
Figure 9G:
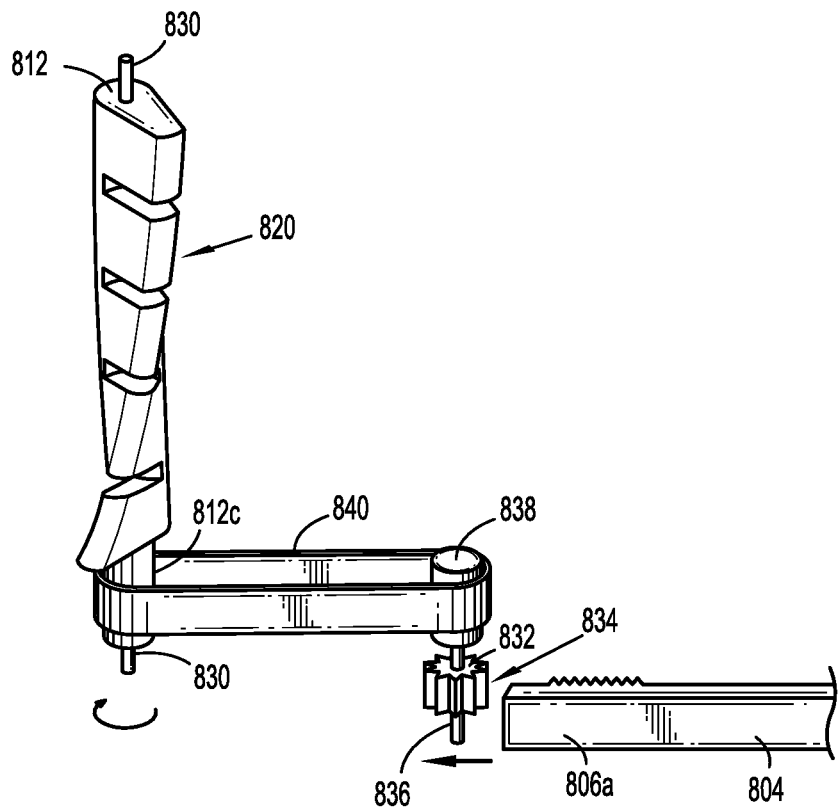
Figure 9H:
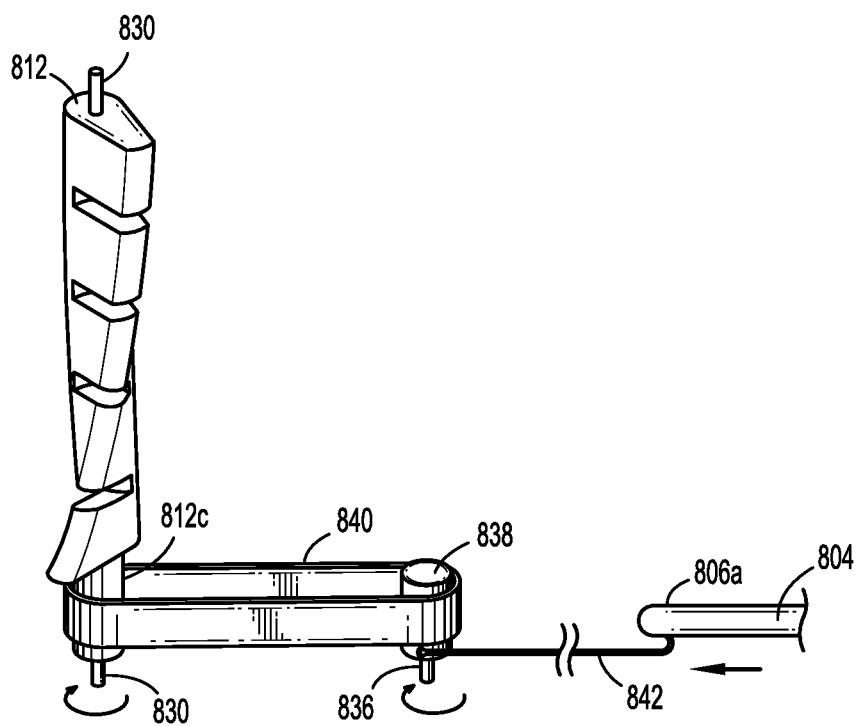
Figure 9I:
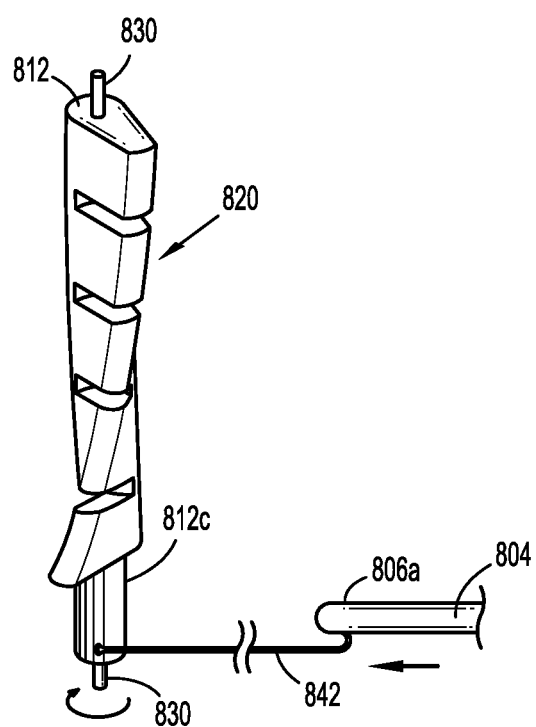
Figure 11A:
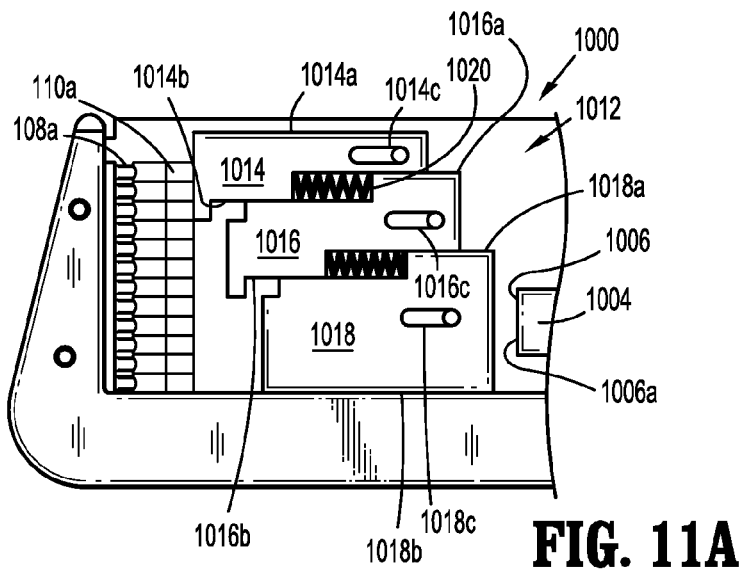
Figure 11B:
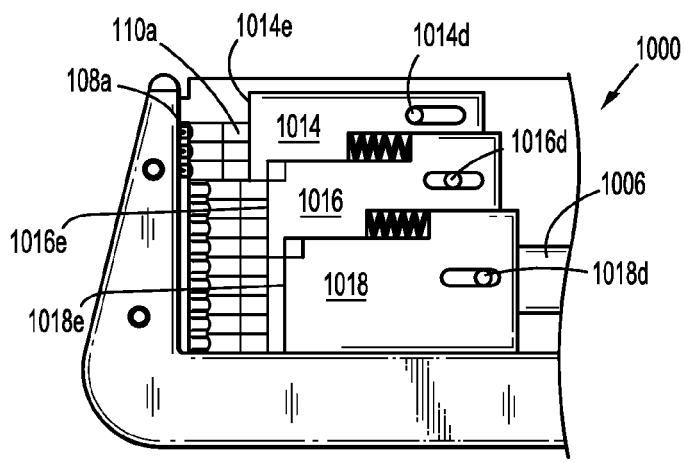
Figure 11C:
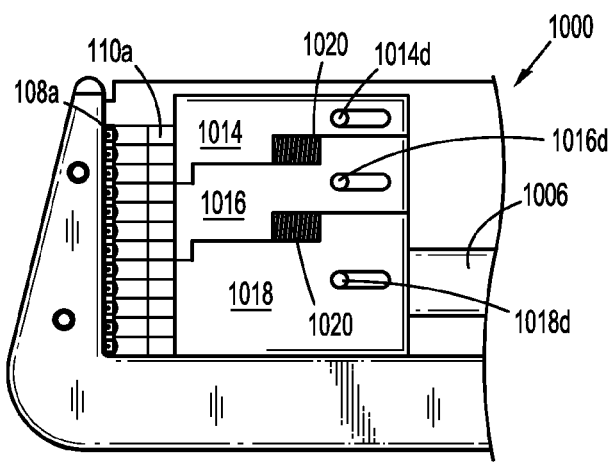
Figure 11D:
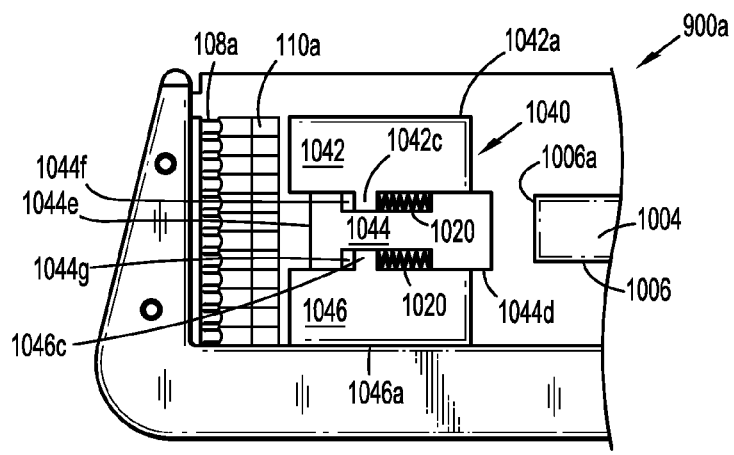
Figure 11E:
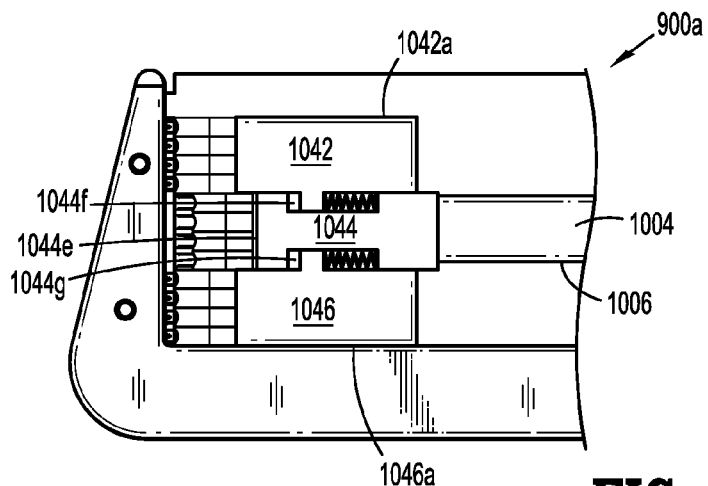
Figure 11F:
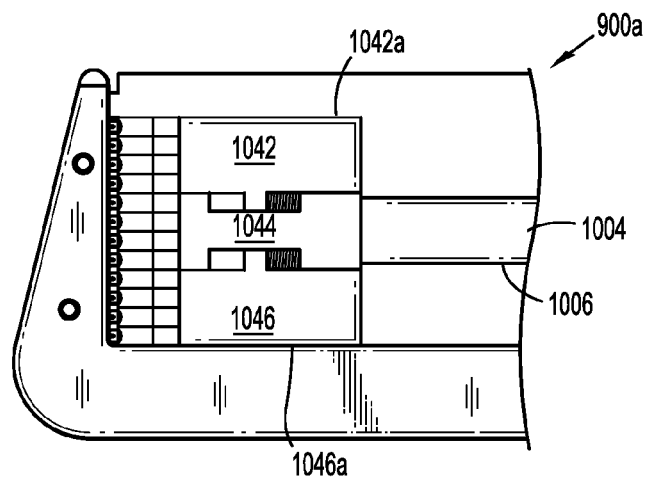
Figure 12A:
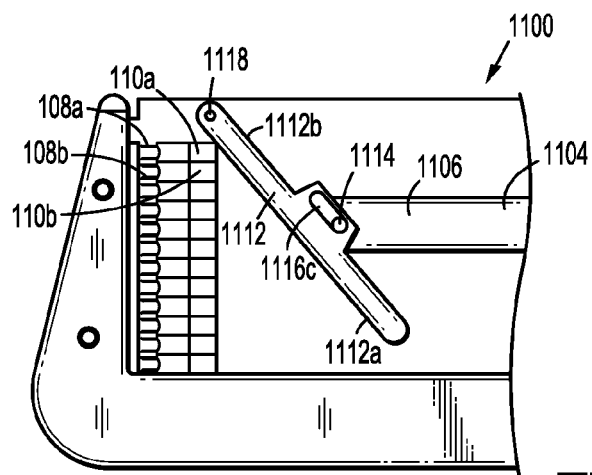
Figure 12B:
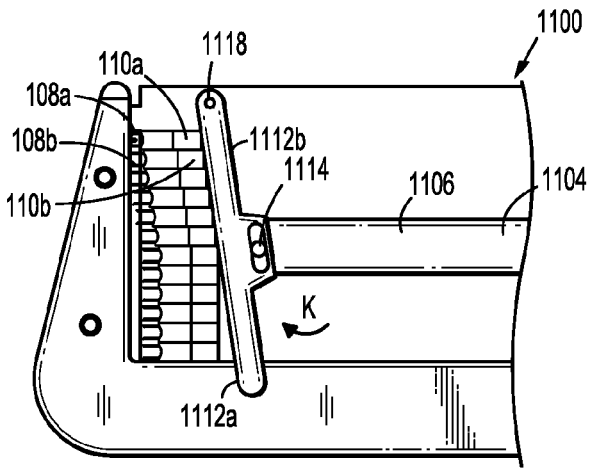
Figure 12C:
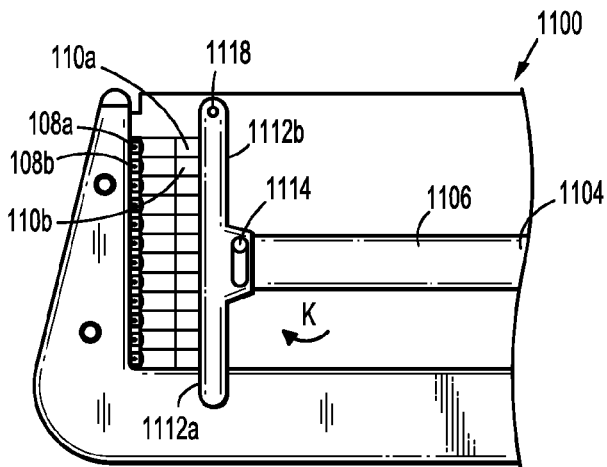
Figure 12D:
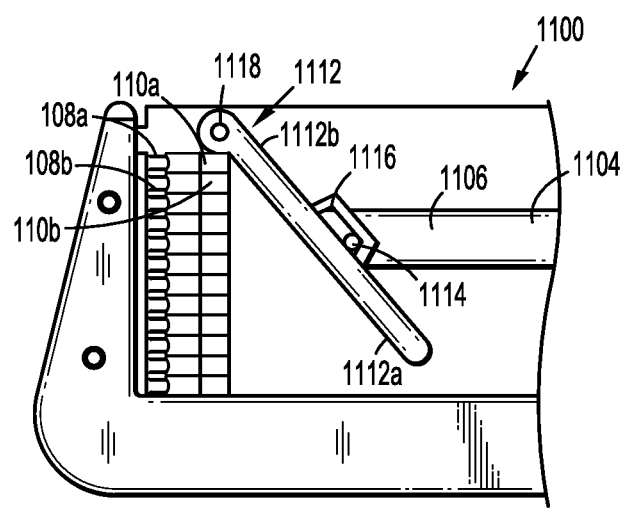
Figure 13A:
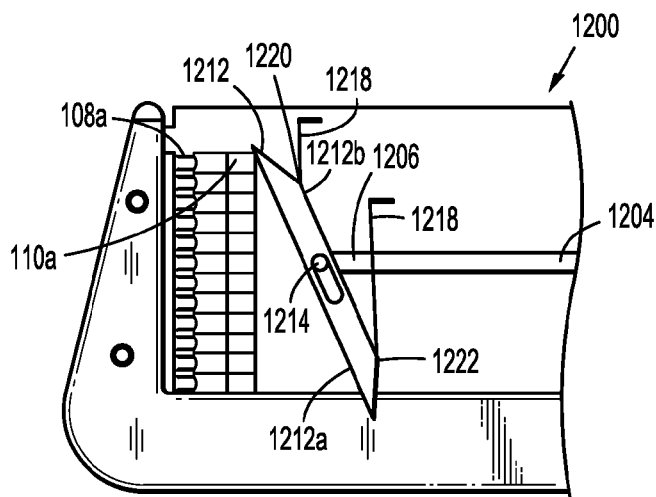
Figure 13B:
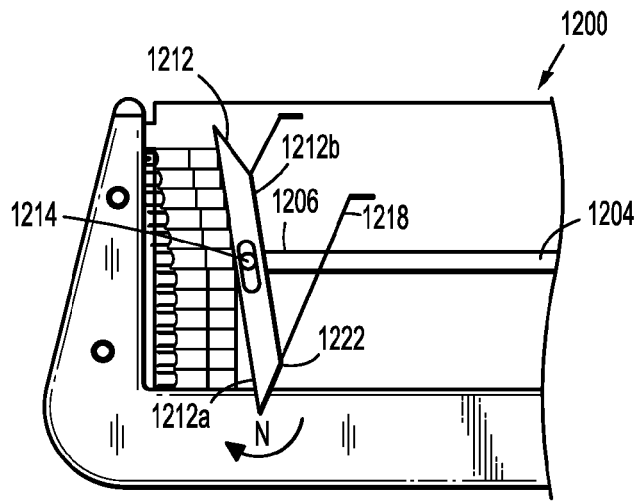
Figure 13C:
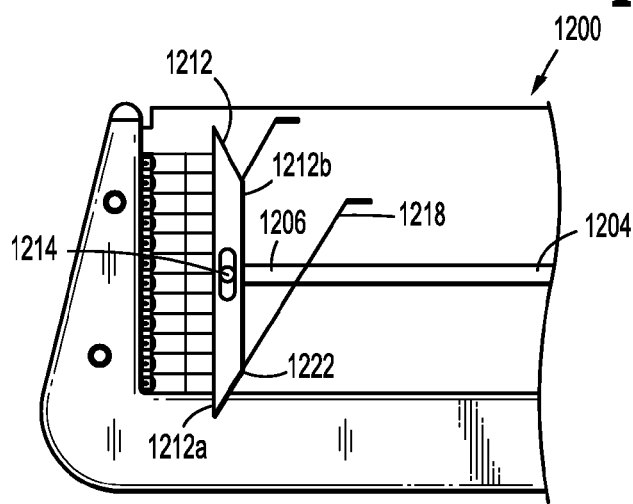

FIG. $6A_{-1}$ is a cut-away view taken along line segment $6A_{-1}$-$6A_{-1}$ of FIG. 6A;

FIG. 6D is a cut away side view of a firing mechanism according to a further embodiment of the present disclosure;

FIGS. 7A-7C are cut-away side views of a firing mechanism that includes a camming configuration in accordance with another embodiment of the present disclosure;

FIGS. 7D-7F are cut-away side views of a firing mechanism that includes a camming configuration in accordance with another embodiment of the present disclosure;

FIGS. 8A-8C are cut-away side views of a firing mechanism that includes a camming configuration in accordance with another embodiment of the present disclosure;

FIGS. 8D-8E are cut-away side views of an alternate camming configuration in accordance with the embodiment depicted in FIGS. 8A-8C;

FIGS. 9A-9C are cut-away side views of a firing mechanism that includes a camming configuration in accordance with another embodiment of the present disclosure;

FIGS. 9D-9F are cut-away side views of a firing mechanism that includes a camming configuration in accordance with another embodiment of the present disclosure;

FIG. 9G is perspective views of various structures configured for rotating the camming configurations depicted in FIGS. 9A-9F;

FIG. 9H is a perspective view of a further structure for rotating the camming configuration according to another embodiment of the present disclosure, shown in a first position;

FIG. 9I is a perspective view of the structure of FIG. 9H, shown in a second position;

FIGS. 10A-10I are cut-away side views of a firing mechanism that includes a camming configuration in accordance with another embodiment of the present disclosure;

FIGS. 11A-11C are cut-away side view of a firing mechanism that includes a camming configuration in accordance with another embodiment of the present disclosure;

FIGS. 11D-11F are cut-away side view of a firing mechanism that includes an alternate embodiment of the camming configuration depicted in FIGS. 11A-11C;

FIG. 12A-12C is a cut-away side view of a firing mechanism that includes a camming configuration in accordance with another embodiment of the present disclosure;

FIG. 12D is a cut away side view of the camming configuration of 12A-12C, shown in another position; and FIG. 13A-13C is a cut-away side view of a firing mechanism that includes a camming configuration in accordance with another embodiment of the present disclosure.

DETAILED DESCRIPTION

Embodiments of the presently disclosed surgical fastener-applying apparatuses are described in detail with reference to the drawings, wherein like reference numerals designate similar or identical elements in each of the several views. In the drawings and the description that follows, the term "proximal" refers to the end of the surgical fastening apparatus that is closest to the operator, whereas the term "distal" refers to the end of the surgical fastening apparatus that is farthest from the operator. As appreciated by one skilled in the art, the depicted surgical fastening apparatus fires fasteners, but it may be adapted to fire any other suitable fastener such as clips and two-part fasteners.

The present disclosure provides a firing mechanism that includes one or more camming configurations that is configured to sequentially fire and deploy each of a plurality of surgical fasteners supported within a cartridge of an end effector assembly of a surgical fastener-applying apparatus.

Figure 1:
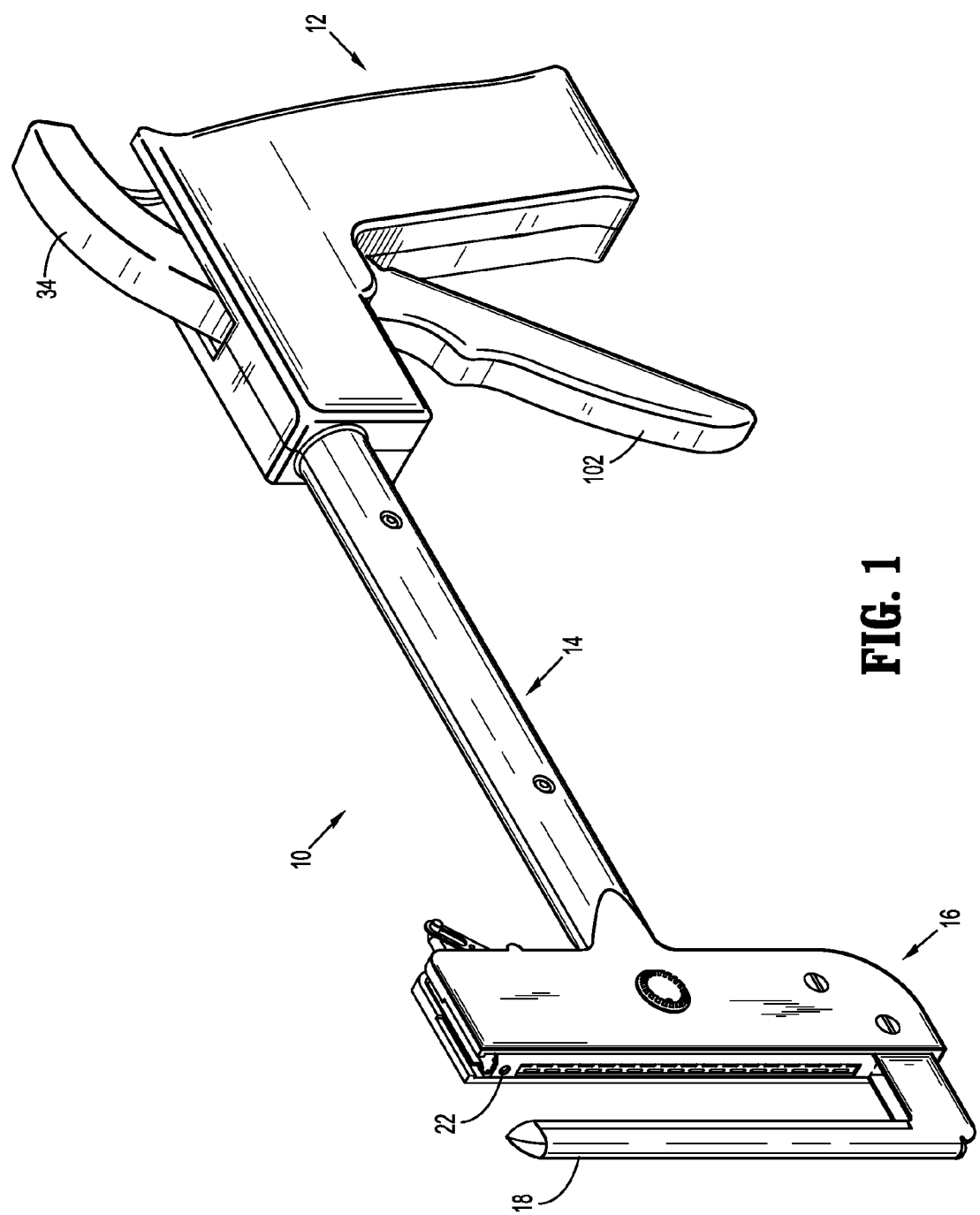
FIG. 1 illustrates a surgical fastening applying instrument including an end effector assembly that employs a firing mechanism for sequentially firing a plurality of surgical fasteners in accordance with embodiments of the present disclosure.

FIG. 1 illustrates one type of surgical fastener-applying apparatus 10 (apparatus 10) that may be employed with a firing mechanism (e.g., 100) of the present disclosure. Apparatus 10 is of the transverse anastomosis type (commonly referred to in the art as "TA" type surgical fastener apparatus available from United States Surgical, a division of Covidien, Norwalk, Conn.) which is often used for stapling a patient's mesentery or omentum. Apparatus 10 includes a handle 12, an elongate portion 14 extending from the handle 12 and an end effector 16. The end effector 16 includes an anvil 18 and a cartridge 22. Apparatus 10 also includes a pivotally mounted approximating clamp 34 for advancing cartridge 22 toward anvil 18, for instance.

For a more detailed explanation of the operation of surgical fastener-applying apparatus 10 and of the approximation of the cartridge with the anvil, reference is made to commonly assigned U.S. Pat. No. 5,964,394 to Robertson, the entire contents of which are incorporated herein by reference.

Figure 2A:
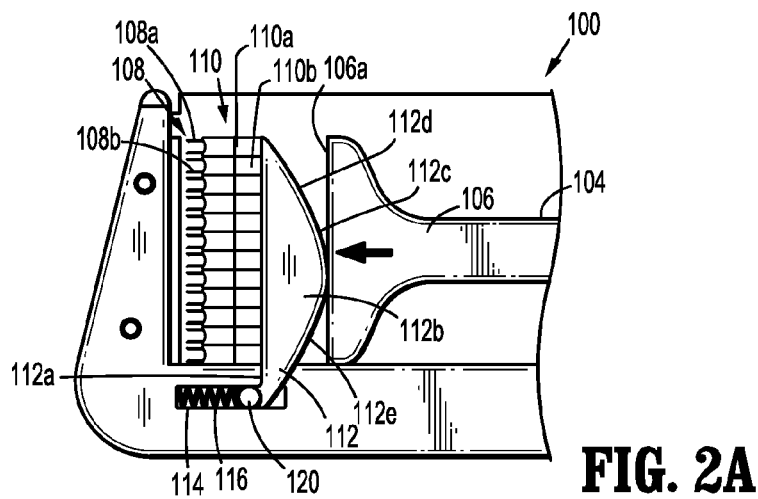
FIGS. 2A-2C are cut-away side views of a firing mechanism that includes a camming configuration in accordance with an embodiment of the present disclosure.
Figure 2B:
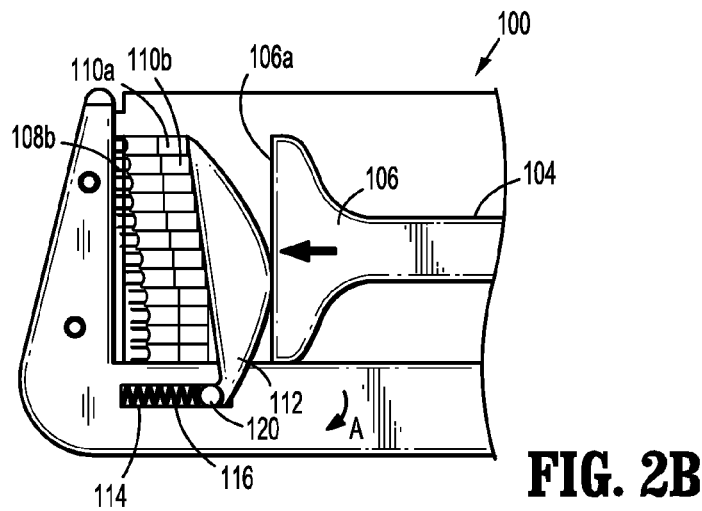
Figure 2C:
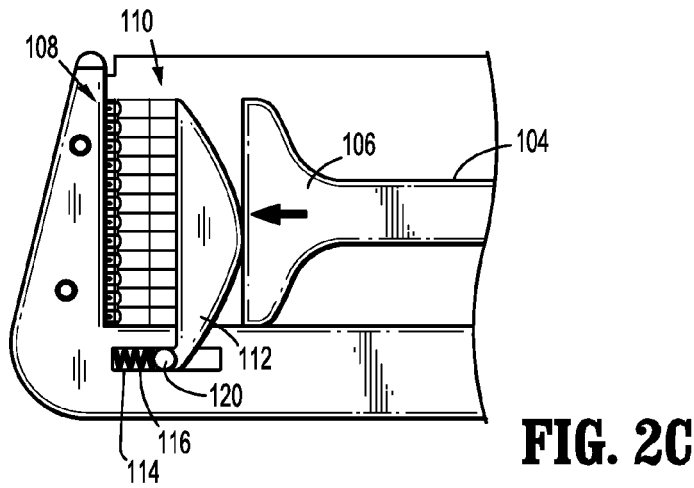

Referring now to FIGS. 2A-2C, and initially with reference to FIG. 2A, an embodiment of the firing mechanism 100 for sequentially applying the fasteners of apparatus 10 is shown. The firing mechanism 100 includes a trigger actuator 102 (see FIG. 1, for example) and an elongate pusher or thrust bar 104 (FIGS. 2A-2C) slidably translatable within elongate portion 14 of the apparatus 10. Trigger actuator 102 is disposed in mechanical cooperation with a proximal end of thrust bar 104 to advance thrust bar 104 distally. For a more detailed description of the trigger actuator 102 and operative features and components associated therewith, reference is again made to U.S. Pat. No. 5,964,394 to Robertson.

A distal end of thrust bar 104 includes a head portion 106 configured to engage at least one pusher 110 to effect ejection of fasteners 108 disposed within cartridge 22. In the embodiments illustrated in FIGS. 2A-2C, head 106 includes a substantially flat distal end 106a that is configured to contact at least a portion of a wedge or cam 112 (cam 112).

Cam 112 is disposed between the head 106 and pusher 110. In the embodiments illustrated in FIGS. 2A-2C, cam 112 includes a distal end 112a and a proximal end 112b. Distal end 112a includes a generally flat configuration. Proximal end 112b includes a proximal concave or curved portion 112c having upper and lower slanted or angled portions 112d, 112e extending distally therefrom to the proximal end 112a. Angled portions 112d, 112e are neither parallel to each other nor distal end 112a. Cam 112 is pivotably connected to a pivot pin or cam pin 120 disposed within a cam slot 114 (slot 114).

Slot 114 may include structure and/or material (e.g., a groove and/or lubricant, not explicitly shown) that facilitates movement of cam 212 therein. A spring 116 (e.g., a torsion spring) is disposed within slot 114 and proximally biases cam pin 120 within slot 114. Slot 114 is dimensioned such that pivot pin 120 is moveable therein from a proximal position to a distal position.

In use, prior to actuation of trigger actuator 102, thrust bar 106 is in an initial proximal position (e.g., start position, see FIG. 2A, for example). Actuation of trigger actuator 102 causes thrust bar 104 to translate distally, which causes head 106 to contact cam 112. The shape of cam 112 in combination with the cam pin 120 force the cam 112 to pivot and rotate counter clockwise (as shown by arrow "A" in FIG. 2B). This rotation of cam 112 causes distal translation of the top most pusher 110a such that pusher 110a contacts its corresponding fastener 108a prior to pusher 110b contacting its corresponding fastener 108b (FIG. 2B), which, in turn, causes the corresponding fastener(s) 108a, 108b to sequentially deploy from the cartridge 22 and toward the anvil 18. As can be appreciated, the cam 112 sequentially contacts the remaining pushers 110, each of which sequentially contacts its corresponding fastener 108. This results in sequential firing of all the fasteners 108.

During deployment of the top most fastener(s) 108 (e.g., 108a, 108b), spring 116 acts to apply pressure to the cam pin 120 keeping the cam pin 120 in place and, thus, preventing the cam 112 from sliding forward. When the cam 112 has rotated to a point where proximal end 112b of the cam 112 and the head 106 of the thrust bar 104 are substantially parallel (as shown in FIG. 2B), the force on the cam 112 overcomes the force exerted by the spring 116. As result thereof, the top pusher(s) (e.g., 110a) that has "bottomed out" (i.e., has completely ejected its corresponding fastener(s) (e.g., 108a)) acts as a second pivot point (FIG. 2B), which, in turn, causes cam 112 to pivot and rotate clockwise (i.e., in the general direction of arrow "B") causing the remaining pushers(s) 110 to be pushed distally, which, in turn, causes the corresponding fastener(s) 108 to deploy from the cartridge 22 and into anvil pocket(s) on the anvil (FIG. 2C).

While the firing mechanism 100 has been described including one or more springs 116, it is within the purview of the present disclosure to have the geometry of the slots 114, pushers 110, cam 112, and/or head 106 of thrust bar 104 designed such that the spring 116 is not needed for the firing mechanism to function as intended.

Figure 3A:
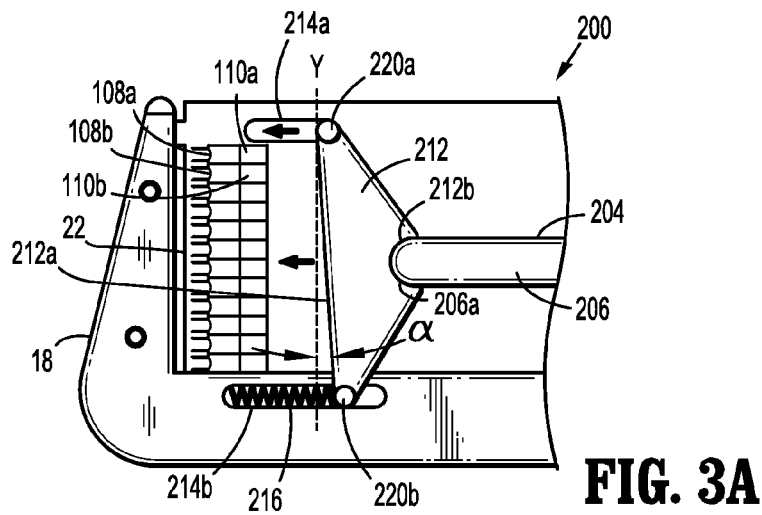
FIGS. 3A-3C are cut-away side views of a firing mechanism that includes a camming configuration in accordance with another embodiment of the present disclosure.
Figure 3B:
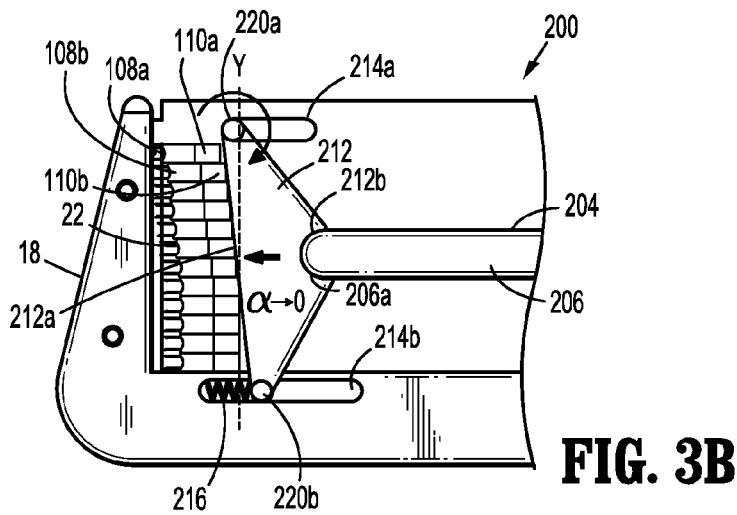
Figure 3C:
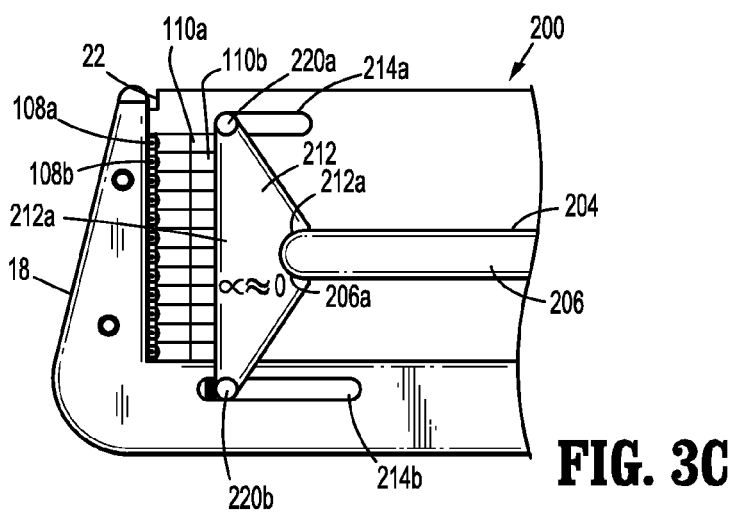

With reference now to FIGS. 3A-3C, and initially with reference to FIG. 3A, an alternate embodiment of a firing mechanism is shown generally as 200 and described. A distal end of thrust bar 204 includes a head portion 206 that includes a substantially curved distal end 206a, which is configured to contact at least a portion of wedge or cam 212. Cam 212 is configured to engage at least one pusher 110 to effect sequential ejection of fasteners 108 disposed within cartridge 22.

Cam 212 is disposed between the head 206 and pushers 110. In the embodiments illustrated in FIGS. 3A-3C, cam 212 includes a substantially flat distal end 212a and includes a proximal end 212b that is configured to receive and/or mechanically engage at least a portion of curved distal end 206a of head 206 such that cam 212 may rotate with respect thereto. In disclosed embodiments, distal end 212a of cam 212 is disposed at an angle α relative to a Y axis (Y-axis is defined by a proximal portion of the pusher(s) 110, see FIG. 3A for example). It is envisioned that angle α decreases as head 206 is distally translated. Cam 212 is pivotably connected to a pair of pivot pins or cam pins 220a, 220b respectively disposed within oversized cam slots 214a and 214b.

Each of slots 214a, 214b may have the same or similar configurations as each other and may include structure and/or material (e.g., a groove and/or lubricant, not explicitly shown) that facilitates movement of cam 212 therein. In the embodiments illustrated in FIGS. 3A-3C, slot 214a has a length that is shorter than a length of slot 214b. A spring 216 (e.g., a torsion spring, a compression spring, etc.) is disposed within slot 214b and proximally biases pivot pin 220b within slot 214b. In embodiments, the spring 216 may also be disposed within slot 214a. Slot 214b is dimensioned such that pivot pin 220 is moveable therein from a proximal position to a distal position and also allows small traverse movement.

In use, prior to actuation of trigger actuator 102, thrust bar 206 is in an initial proximal position (e.g., start position, see FIG. 3A, for example). Actuation of trigger actuator 102 causes thrust bar 204 to translate distally, which causes head 206 to translate distally which causes cam 212 to translate distally. The shape and initial angle α (relative to proximal portion of the pusher(s) 110) of cam 212 in combination with the pivot pins 220a, 220b, and spring 216 causes cam 212 to translate within slot 214a. This translation of cam 212 causes the top most pusher 110a forward to contact its corresponding fastener 108a prior to pusher 110b contacting its corresponding fastener 108b (FIG. 3B), which, in turn, causes the corresponding fastener(s) 108a, 108b to sequentially deploy from the cartridge 22 and toward the anvil 18. As can be appreciated, the cam 212 sequentially contacts the remaining pushers 110, each of which sequentially contacts its corresponding fastener 108. This results in sequential firing of all the fasteners 110.

During deployment of the top most fastener(s) 108 (e.g., 108a, 108b), spring 216 acts to apply pressure to pivot pin 220b keeping the pivot pin 220b in place and, thus, preventing a bottom portion of the cam 112 from sliding or translating forward. When the upper pivot pin 220a of cam 212 has translated to a point within the slot 214a (e.g., a distal most end of slot 214, as shown in FIG. 3B) where it is prevented from further translating, the force on the cam 212 exerted by the thrust bar 204 overcomes the force exerted on the pivot pin 220b by the spring 216. As a result thereof, cam 212 pivots about the pivot pin 220a causing the bottom portion of the cam 212 to pivot and rotate clockwise (i.e., in the direction of arrow "C" (angle α approaches 0°)), and the pivot pin 220b to translate forward within the slot 214b causing the remaining pushers(s) 110 to be pushed distally, which, in turn, causes the corresponding fastener(s) 108 to deploy from the cartridge 22 and into the anvil pocket(s) on the anvil (FIG. 3C). When the last fastener(s) 108 have been deployed angle α is ≈0°. In other embodiments (not explicitly shown), angle α is less than 0°.

Figure 3D:
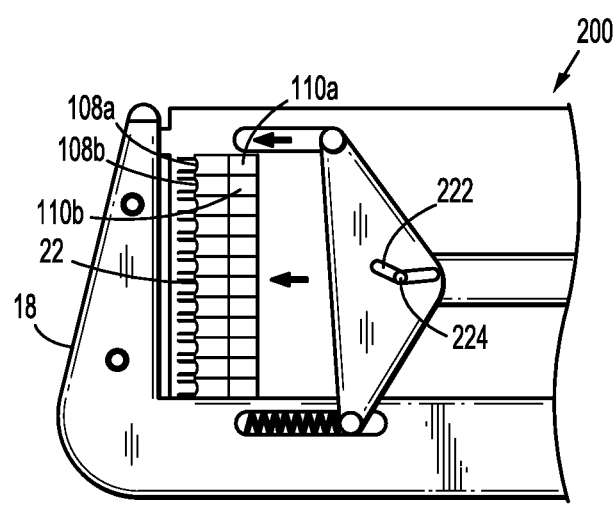
FIG. 3D is cut-away side view of a firing mechanism that includes an alternate camming configuration in accordance with the embodiment depicted in FIGS. 3A-3C.

While the embodiment depicted in FIGS. 3A-3C illustrates head 206 of thrust bar 204 including a substantially curved configuration, it is within the purview of the present disclosure to have head 206 operatively coupled to cam 212 by way of a slot and pin configuration (see FIG. 3D for example). In this instance, for example, cam 212 may include a curved or angled slot 222 that is operatively disposed thereon and configured to mechanically engage thrust bar 204 by way of a pivot pin or cam pin 224 associated therewith.

Additionally, while the firing mechanism 200 has been described including one or more springs 216, it is within the purview of the present disclosure to have the geometry of the slots 214, pushers 110, cam 212, and/or head 206 of thrust bar 204 designed such that a spring 216 is not needed for the firing mechanism to function as intended.

Figure 3E:
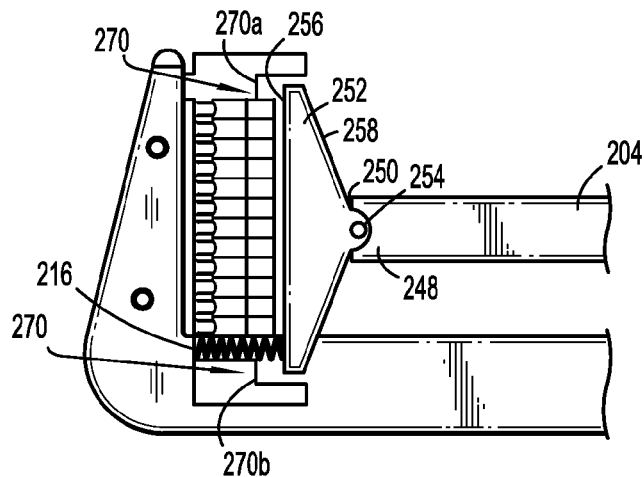
FIGS. 3E-3G are cut-away side view of a firing mechanism that includes a camming configuration in accordance with another embodiment of the present disclosure.
Figure 3F:
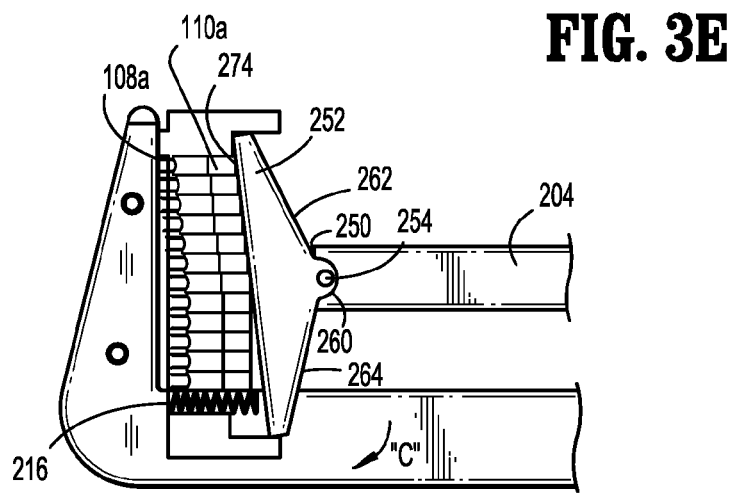
Figure 3G:
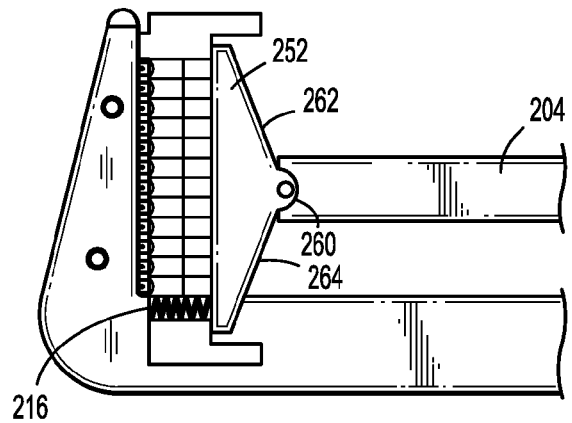

With reference to FIGS. 3E-3G, an alternate camming configuration of the embodiment depicted in FIGS. 3A-3D is shown. In the embodiments illustrated in FIGS. 3E-3G, a distal end of thrust bar 204 includes a head portion 248 that includes a generally flat distal end 250, which is configured to contact at least a portion of wedge or cam 252. In disclosed embodiments, flat distal end 250 is configured to function as an articulation limiter. That is, the flat distal end 250 is configured to contact a portion of the cam 252 which, in turn, prevents the cam 252 from articulating, to be described in greater detail below. In the embodiment illustrated in FIGS. 3E-3G, distal end 250 is pivotably coupled to the cam 252 via a pivot pin 254 or the like.

Cam 252 is configured to engage at least one pusher 110 to effect sequential ejection of fasteners 108 disposed within cartridge 22. To this end, cam 252 is disposed between the head 248 and pushers 110. In the embodiments illustrated in FIGS. 3E-3G, cam 252 includes a substantially flat distal end 256 and includes a proximal end 258 that is configured to receive and/or mechanically engage at least a portion of flat distal end 250 of head 248 such that cam 252 may rotate with respect thereto. Proximal end 258 includes upper and lower slanted or angled portions 262, 264 culminating at a proximal tip 260 that couples to the distal end 250 of the head portion 248 (FIG. 3F). Proximal tip 260 operably couples to the distal end 256 via pivot pin 254. During articulation of the cam 252 each of the angled portions 262, 264 contact a portion of the flat distal end 250 (see FIG. 3F, for example). Contact between either of the angled portions 262, 264 and flat distal end 250 prevents articulation of the cam 252 in a clockwise and/or counter clockwise direction, respectively. More particularly, when angled portion 262 contacts the flat distal end 250, cam 252 is prevented from articulating in a clockwise direction and when angled portion 264 contacts the flat distal end 250, cam 252 is prevented from articulating in a counterclockwise direction. In the embodiment illustrated in FIGS. 3E-3G, each of slots 214a, 214b may be replaced by one or more cam stops 270 (an upper cam stop 270a and lower cam stop 270b are shown) operatively disposed at predetermined locations on or adjacent cartridge 22. Each of the upper and lower cam stops 270a and 270b, respectively, is configured to impede and/or prevent distal movement of respective upper and lower portions 230 and 240 of cam 211. A spring 216 (e.g., a torsion spring, a compression spring, etc.) is disposed within a slot 214d and proximally biases a lower portion 240 of cam 212.

In use, when an upper portion 274 of cam 262 contacts an upper cam stop 270a (FIG. 3F) upper portion 274 is prevented from further translating, the force on the cam 252 exerted by the thrust bar 204 overcomes the force exerted on lower portion 276 of cam 252 by spring 216. As a result thereof, cam 252 pivots about a portion of upper cam stop 270a causing the bottom portion 274 of the cam 212 to pivot and rotate clockwise (i.e., in the direction of arrow "$C_1$"), and the bottom portion of the cam 252 is caused to translate forward causing the remaining pushers(s) 110 to be pushed distally, which, in turn, causes the corresponding fastener(s) 108 to deploy from the cartridge 22 and into the anvil pocket(s) on the anvil (FIG. 3G). As described previously herein with respect to FIG. 3C, when the last fastener(s) 108 have been deployed angle α is ≈0°. In other embodiments (not explicitly shown), angle α is less than 0°.

Figure 3H:
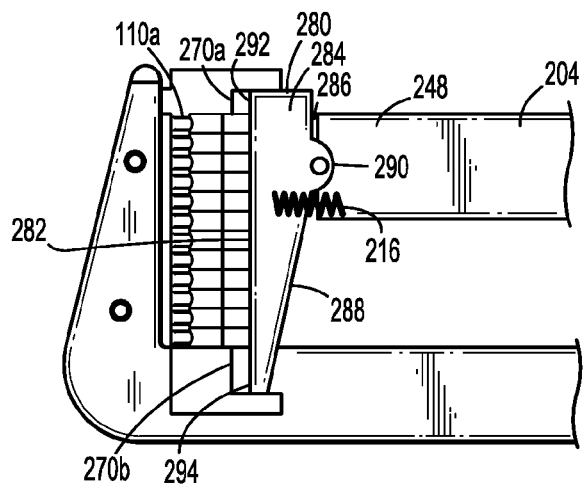
FIGS. 3H-3J are cut-away side view of a firing mechanism that includes a camming configuration in accordance with another embodiment of the present disclosure.
Figure 3I:
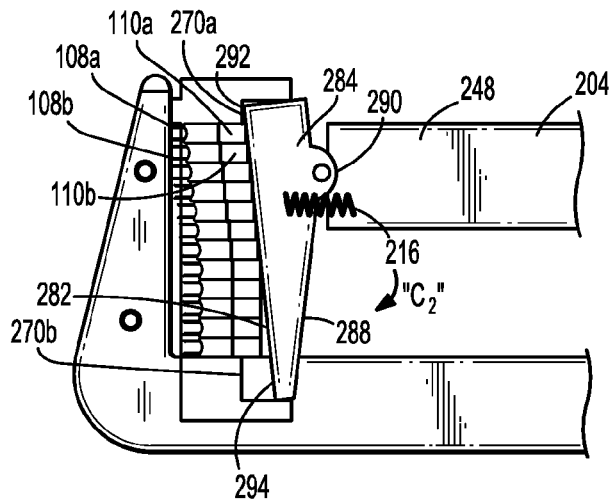

While the embodiment depicted in FIGS. 3E-3G illustrates spring 216 operatively associated with lower cam stop 270$_b$, it is within the purview of the present disclosure to have a spring 216 operatively coupled to both a portion of a cam 280 and the thrust bar 204 (see FIG. 3H, for example). In the embodiment illustrated in FIGS. 3H-3J, thrust bar 204 is operatively connected to an upper portion of a cam 280 and spring 216 may be operably disposed below the pivot pin 254; this configuration, causes the top most pusher 110a forward to contact its corresponding fastener 108a prior to pusher 110b contacting its corresponding fastener 108b (FIG. 3I). Conversely, thrust bar 204 may be operatively connected to a lower portion (not explicitly shown) of the cam 280 and spring 216 may be disposed above the pivot pin 254; this configuration, causes the top most pusher 110a forward to contact its corresponding fastener 108a prior to pusher 110b contacting its corresponding fastener 108b.

Cam 280 is configured to engage at least one pusher 110 to effect sequential ejection of fasteners 108 disposed within cartridge 22. To this end, cam 280 is disposed between a head 248 and pushers 110. In the embodiments illustrated in FIGS. 3H-3J, cam 280 includes a substantially flat distal end 282 and includes a proximal end 284 that is configured to receive and/or mechanically engage at least a portion of flat distal end 250 of head 248 such that cam 280 may rotate with respect thereto. Proximal end 284 includes an upper portion 286 having a substantially flat configuration and lower portion 288 having a slanted or angled configuration. A proximal tip 290 couples to the distal end 250 of the head portion 248. Proximal tip 290 operably couples to the distal end 256 via pivot pin 254. During articulation of the cam 280 each of upper and lower portions 286 and 288, respectively, contact a portion of the flat distal end 250 (see FIG. 3I, for example). Contact between either of the upper and lower portions 286 and 288, respectively, and flat distal end 250 prevents articulation of the cam 280 in a clockwise and/or counter clockwise direction. More particularly, when upper portion 286 contacts the flat distal end 250, cam 280 is prevented from articulating in a clockwise direction and when lower portion 288 contacts the flat distal end 250, cam 280 is prevented from articulating in a counter-clockwise direction. In the embodiment illustrated in FIGS. 3H-3I, one or more cam stops 270 (an upper cam stop 270a and lower cam stop 270b are shown) is operatively disposed at predetermined locations on or adjacent cartridge 22. Each of the upper and lower cam stops 270a and 270b, respectively, is configured to impede and/or prevent distal movement of respective upper and lower portions 292 and 294 of cam 280.

Figure 3J:
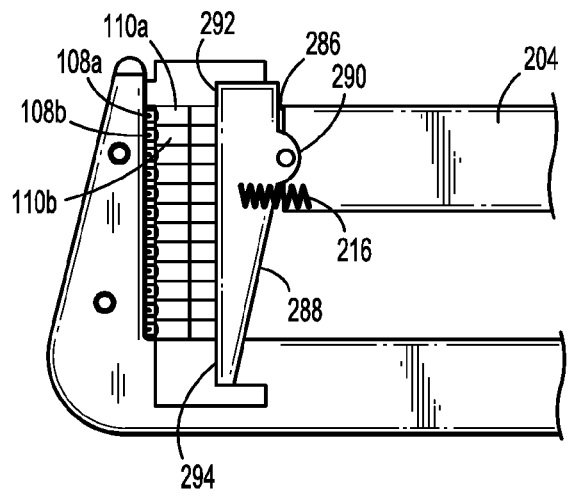

In use, when upper portion 292 of cam 252 contacts an upper cam stop 270a (FIG. 3I) upper portion 292 is prevented from further translating, the force on the cam 280 exerted by the thrust bar 204 overcomes the force exerted on the lower portion 288 of cam 280 by a spring 216. As a result thereof, cam 280 pivots about a portion of upper cam stop 270a causing the bottom portion of the cam 280 to pivot and rotate clockwise (i.e., in the direction of arrow "$C_2$", as shown in FIG. 3I), and the bottom portion of the cam 294 is caused to translate forward causing the remaining pushers(s) 110 to be pushed distally, which, in turn, causes the corresponding fastener(s) 108 to deploy from the cartridge 22 and into the anvil pocket(s) on the anvil (FIG. 3J). As described previously herein with respect to FIGS. 3C and 3G, when the last fastener(s) 108 have been deployed angle α is ≈0°. In other embodiments (not explicitly shown), angle α is less than 0°.

Figure 4A:
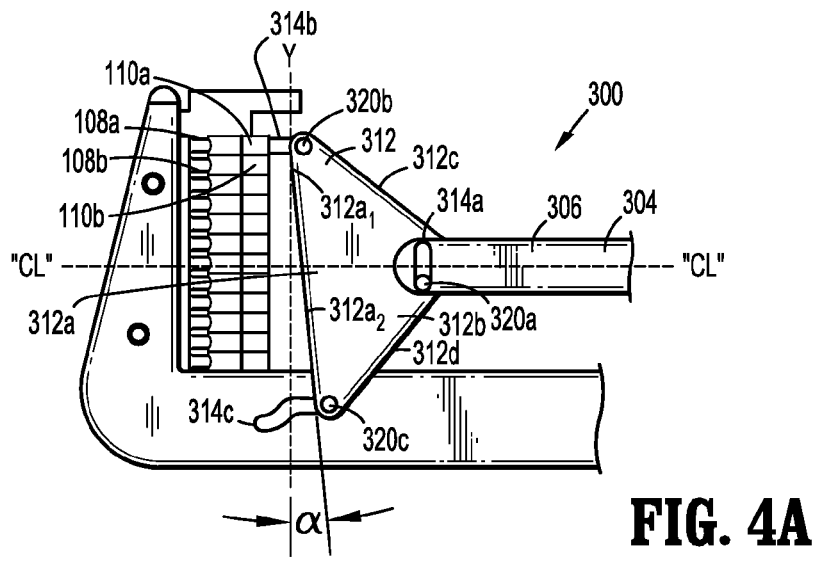
FIGS. 4A-4C are cut-away side views of a firing mechanism that includes a camming configuration in accordance with another embodiment of the present disclosure.
Figure 4B:
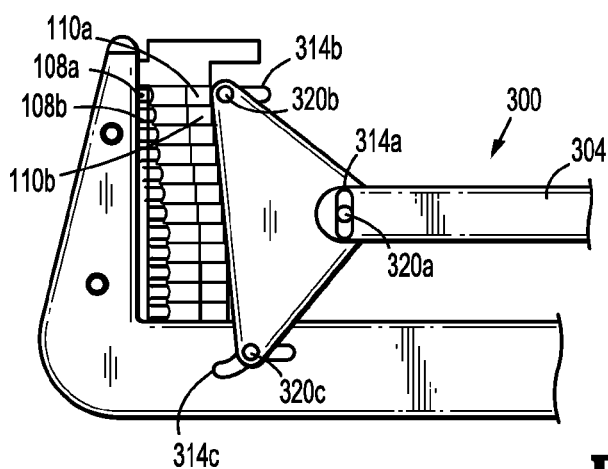
Figure 4C:
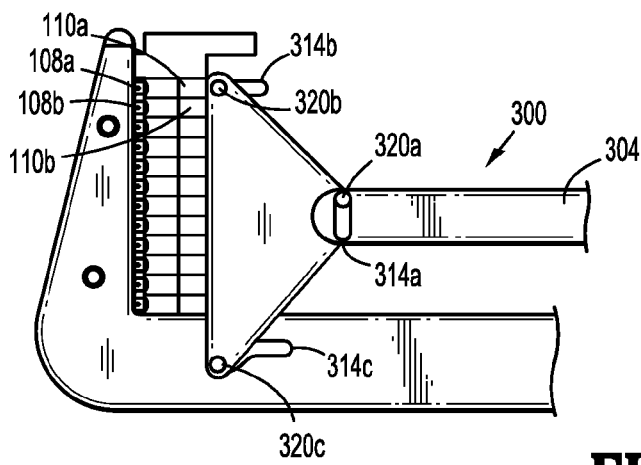

With reference now to FIGS. 4A-4C, and initially with reference to FIG. 4A, an alternate embodiment of a firing mechanism is shown generally as 300 and described.

A distal end of thrust bar 304 includes a head portion 306 that is configured to cause at least one pusher 110 to effect ejection of fasteners 108 disposed within cartridge 22. In the embodiments illustrated in FIGS. 4A-4C, thrust bar 304 includes a distal end 306 that operably couples to at least a portion of a wedge or cam 312 (cam 312). Distal end 306 includes a vertical slot 314a configured to receive one or more pivot pins or cam pins 320a operably associated with the cam 312. Alternatively, the distal end may couple to cam 312 in a manner as described hereinabove with respect to FIGS. 3A-3C.

Cam 312 is disposed between the thrust bar 304 and pushers 110. In the embodiments illustrated in FIGS. 4A-4C, cam 312 includes a distal end 312a having an upper portion 312$a_1$, and a lower portion 312$a_2$. For illustrative purposes, upper portion 312$a_1$ and a lower portion 312$a_2$ are shown separated by imaginary center-line "CL." Cam 312 also includes a proximal end 312b includes upper and lower slanted or angled portions 312c, 312d. Cam 312 includes cam pin 320a that is in mechanical communication with the slot 314a of the end 306a such that cam 312 may rotate with respect thereto. Distal end 312a of cam 312 is disposed at an angle α' relative to a Y' axis (Y'-axis is defined by a proximal portion of the pusher(s) 110, see FIG. 4A for example). It is envisioned that angle α' decreases as head 306 is distally translated. Cam 312 is pivotably connected to one or more pivot pins or cam pins 320b, 320c disposed respectively within one or more cam slots 314b and 314c.

In the embodiment illustrated in FIGS. 4A-4C, slots 314b and 314c are disposed at predetermined locations within end effector 16. Each of slots 314b and 314c include proximal and distal ends, with the proximal and distal ends of slot 314c being longitudinally offset from each other, the operation of which to be described in more detail below. Slot 314c is slanted or angled and is located on cam 312 adjacent to the lower portion 312$a_2$. Each of slots 314b and 314c is dimensioned such that pivot pins 320b, 320c and/or cam 312 or portion thereof is moveable therein from a proximal position to a distal position. Although not explicitly shown, it is envisioned that one or more suitable types of springs may be disposed within any of the slots 314a, 314b and 314c.

In use, prior to actuation of trigger actuator 102, thrust bar 304 is in an initial proximal position (e.g., start position, see FIG. 4A, for example). In the start position, cam pin 320a is in an initial, bottom position located within the slot 314a. Actuation of trigger actuator 102 causes thrust bar 304 to translate distally, which causes cam 312 to translate distally within slot 314b. The shape and initial angle α' (relative to proximal portion of the pusher(s) 110) of cam 312 in combination with the cam pins 320b and 320c and slot configuration, causes the top portion 312$a_1$ of cam 312 to translate within slot 314b and the bottom portion 312$a_2$ to slide within the cam slot 314c. This translation of top portion 312$a_1$ of cam 312 causes the top most pusher 110a forward to contact its corresponding fastener 108a prior to pusher 110b contacting its corresponding pusher 110b (FIG. 4B), which, in turn, causes the corresponding fastener(s) 108a, 108b to sequentially deploy from the cartridge 22 and toward the anvil 18. As can be appreciated, the cam 312 sequentially contacts the remaining pushers 110, each of which sequentially contacts its corresponding fastener 108. This results in sequential firing of all the fasteners 110. During translation of the top portion 312$a_1$ and prior to the top fastener fully forming or "bottoming out" the angle α' remains relatively constant.

When the upper cam pin 320b of cam 312 has translated to a point within the slot 314b (e.g., a distal most end of slot 314b, as shown in FIG. 4B) where it is prevented from further translating, the force on the cam 312 exerted by the thrust bar 304 overcomes the force exerted on the cam pin 320c by the lower slot geometry (e.g., slot 314c). As a result thereof, cam 312 pivots about the cam pin 320a causing the bottom portion 312$a_2$ of the cam 312 to pivot and rotate clockwise (i.e., in the direction of arrow "D" (angle α' approaches 0°)), and the pivot pin 320b to translate forward within the slot 314c causing the remaining pushers(s) 110 to be pushed distally, which, in turn, causes the corresponding fastener(s) 108 to deploy from the cartridge 22 and into the anvil pocket(s) on the anvil (FIG. 4C). It is envisioned that when the last fastener(s) 108 have been deployed, angle α' is ≈0°.

Figure 5A:
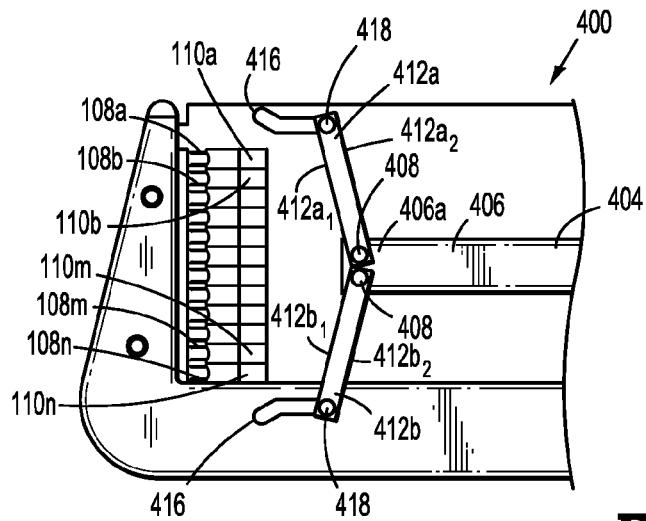
FIGS. 5A-5C are cut-away side views of a firing mechanism that includes a camming configuration in accordance with another embodiment of the present disclosure.
Figure 5B:
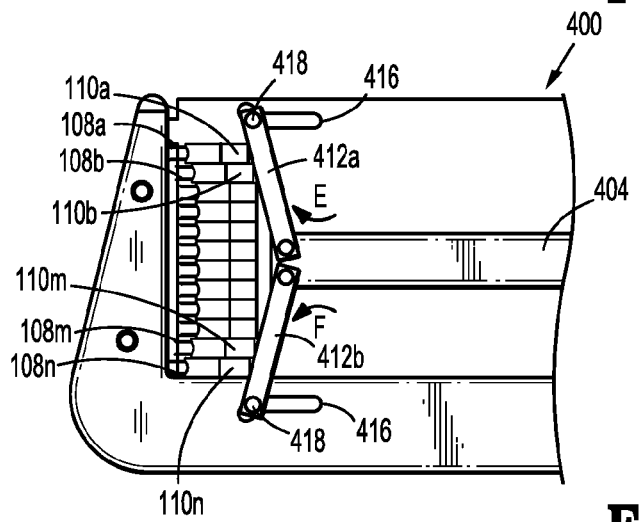
Figure 5C:
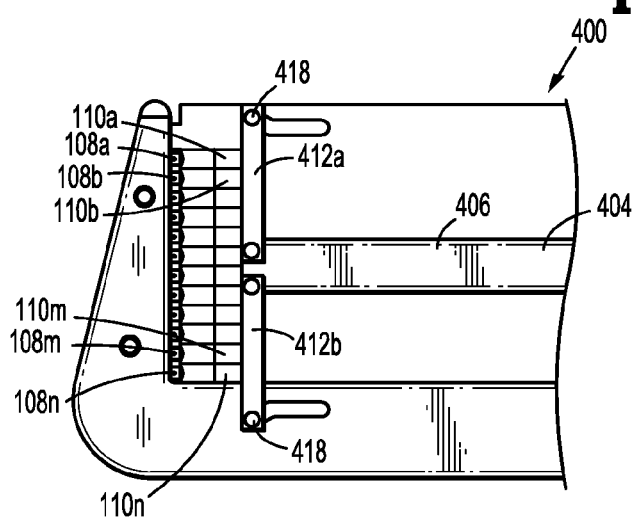

With reference now to FIGS. 5A-5C, and initially with reference to FIG. 5A, an alternate embodiment of a firing mechanism is shown generally as 400 and described.

A distal end of thrust bar 404 includes a head portion 406 configured to engage at least one pusher 110 to effect ejection of fastener(s) 108 disposed within cartridge 22. In the embodiments illustrated in FIGS. 5A-5C, head 406 includes a distal end 406a that is configured to operatively couple to one or more links 412 (two links 412a, 412b are shown). With this purpose in mind, distal end 406a includes one or more pivot pins or cam pins 408 (two cam pins 408 are shown) that operatively couple to the links 412.

Each of links 412a, 412b is disposed between the head 406 and pushers 110. Each of the links 412a, 412b includes a respective distal pusher contacting surface 412$a_1$, 412$b_1$, and a proximal surface 412$a_2$, 412$b_2$ that mechanically engages distal end 406a of head portion 406. In embodiments, for example, one or more pivot pins 408, rivets, etc. mechanically couples each of proximal surfaces 412$a_2$, 412$b_2$ to distal end 406a. Each link 412a, 412b is pivotably connected to a cam pin or pivot pin 418 disposed within a respective cam slot 416 (slots 416).

Each of slots 416 may have the same or similar configurations and/or geometries as each other and may include structure and or material (e.g., a groove and/or lubricant, not explicitly shown) that facilitates movement of links 412a, 412b therein. Slots 416 are located at predetermined positions within the end effector 16. Slots 416 each include proximal and distal ends 416a, 416b. In embodiments, slots 416 may include a portion that is bent, arcuate or curved near or at a distal end thereof. One or more springs (e.g., spring 116) may be disposed within each of the slots 416. Each of slots 416 is dimensioned such that pivot pins 418 and/or links 412a, 412b, or portions thereof, are moveable therein between a proximal position to a distal position.

In use, prior to actuation of trigger actuator 102, thrust bar 406 is in an initial proximal position (e.g., start position, see FIG. 5A, for example). Proximal translation of trigger actuator 102 causes thrust bar 404 to translate distally, which causes the cam pins 418 and the links 412a, 412b to translate within the slots 416. This translation of the cam pins 418 and the links 412a, 412b causes the outer most pusher(s) (e.g., 110a, 110n) distally to contact their corresponding outer most fastener(s) (e.g., 108a, 108n) prior to pusher(s) 110b, 110m contacting their corresponding pushers 110b, 108m (FIG. 4B), which, in turn, causes the corresponding fastener(s) 108a, 108n to substantially simultaneously deploy from the cartridge 22 and toward the anvil 18. As can be appreciated, the links 412 sequentially contact the remaining pushers 110, each of which sequentially contacts its corresponding fastener 108.

When the pivot pins 418 of links 412a, 412b have translated to a point within the slots 416 where they are prevented from further translating (e.g., a distal most end of slots 416), the force exerted on the links 412a, 412b by thrust bar 404 causes the links 412a, 412b to pivot about the pivot pins 418. As a result thereof, the links 412a, 412b rotate clockwise (i.e., in the direction of arrow "E") and counter clockwise (i.e., in the direction of arrow "F"), respectively, causing the remaining pushers(s) 110 to be pushed distally (from the outermost pusher(s) 110 to the middle pusher(s) 110), which, in turn, causes the corresponding fastener(s) 108 to deploy from the cartridge 22 and into the anvil pocket(s) on the anvil 18 (FIG. 5C).

With reference now to FIGS. 6A-6C, and initially with reference to FIG. 6A, an alternate embodiment of a firing mechanism is shown generally as 500 and described.

A distal end of thrust bar 504 includes a head portion 506 in mechanical communication with at least two sets of pushers 110a and 110b to effect ejection of two sets of corresponding fasteners 108a and 108b disposed within cartridge 22 (as best seen in FIG. 6B). Head portion 506 is positioned within an upper half of the cartridge 22. In the embodiments illustrated in FIGS. 6A-6C, a distal end 506a of head portion 506 is configured to function as a rack in a rack and pinion configuration. To this end, distal end 506a includes a plurality of teeth 508a that are configured to engage or mesh with a plurality of teeth 508b operatively associated with a driving disc 510 (configured to function as a pinion in a rack and pinion configuration) operatively disposed within the cartridge 22. In the embodiment illustrated in FIGS. 6A-6C, the plurality of teeth 508a is positioned on a bottom portion of the head 506. Alternatively, the plurality of teeth 508a may be positioned on a top portion of the head 506; this configuration of the plurality of teeth 508a on the top portion of the head 506 is suitable when the head portion 506 is positioned within a lower half of the cartridge 22.

Driving disc 510 may include any suitable geometric configuration. In the embodiment illustrated in FIGS. 6A-6C, driving disc 510 includes a generally circumferential configuration. Driving disc 510 includes two generally circumferential opposing side surfaces 516, 518. Driving disc 510 is configured to rotate against a frame that supports the cartridge 22. To this end, driving disc 510 includes an offset, generally circumferential gear wheel 512 including a plurality of teeth 508b. Gear wheel 512 is operably disposed along one of the side surfaces 516, 518 of driving disc 510 (gear wheel 512 is shown disposed along side surface 516). The gear wheel 512 is configured such that as thrust bar 504 is translated distally, the plurality of teeth 508a at the distal end 506a engage or mesh with the plurality of teeth 508b on the gear wheel 512. A first drive pin 520 is operatively disposed on side surface 516 and a second drive pin 522 is operatively disposed on side surface 518. The drive pins 520, 522 are configured to transfer the rotational motion of the drive disc 510 to a yoke mechanism 524. First drive pin 520 is located adjacent a peripheral edge of the driving disc 510 (FIG. 6A). Likewise, second drive pin 522 is located adjacent a peripheral edge of the driving disc 510 (FIG. 6A). The first drive pin 520 is movable from a first position, wherein the first drive pin 520 is positioned distally relative to the second drive pin 522 (FIG. 6A), to a subsequent or final position, wherein the first drive pin 520 is positioned proximally relative to the second drive pin 522 (FIG. 6C).

Yoke mechanism 524 is in mechanical communication with the driving disc 510 and the pushers 110a and 110b. More particularly, the yoke mechanism includes a first cam member or slide 526 and a second cam member or slide 528 that are movable with respect to each other and configured to contact a respective set of pushers 110a and 110b (as best seen in FIG. 6B). To this end, each of the first and second slides 526 and 528, respectively, includes a distal, substantially flat pusher contacting surface 526a and 528a. The first slide 526 and second slide 528 are movably disposed laterally and longitudinally offset from each other. More particularly, the first slide 526 is movable from an initial position, wherein the first slide is positioned distally relative to the second slide 528 (as best seen in FIG. 6A), to a subsequent or final position, wherein the first slide 526 is positioned proximally relative to the second slide 528 (as best seen in FIG. 6C). The first slide 526 operably couples to the first drive pin 520 and the second slide 528 operatively couples to the second drive pin 522 (FIG. 6A-1). The first slide 526 is in operative communication with the first set of pushers 110a and the second slide 528 is in operative communication with the second set of pushers 110b, such that rotation of the driving disc 510 rotates the drive pins 520 and 522, which, in turn, translates a respective slide 526 and 528 distally toward a respective pusher 110a and 110b. More particularly, the first slide 526 is configured to contact pusher 110a, which, in turn, causes a corresponding plurality of fasteners 108a to deploy from the cartridge 22 and into the anvil pocket(s) on the anvil. Similarly, second slide 528 is configured to contact pusher 110b, which, in turn, causes a corresponding plurality of fasteners 108b to deploy from the cartridge 22 and into the anvil pocket(s) on the anvil.

In use, prior to actuation of trigger actuator 102, thrust bar 504 is in an initial proximal position (e.g., start position, see FIG. 6A). Actuation of trigger actuator 102 causes thrust bar 504 to translate distally, which causes the plurality of teeth 508a to contact the plurality of teeth 508b causing the driving disc 510 to rotate in a counter-clockwise direction (see FIG. 6B, for example). As driving disc 510 rotates, first and second drive pins 520 and 522, respectively, cause a respective slide 526 and 528 to translate distally toward the respective set of pushers 110a and 110b. The spacing configuration of the slides 526 and 528 in combination with the positioning of the first and second drive pins 520 and 522, respectively, on the driving disc 510 facilitate in forming the set of surgical fasteners 108a first, and subsequently deploying and forming the set of surgical fasteners 108b next. More particularly, because the first slide 526 is positioned distal the slide 528, first slide 526 contacts the set of pushers 110a prior to the second slide 528 contacting the set of pushers 110b. Thus, the set of fasteners 108a deploy from the cartridge 22 and into the anvil pocket(s) on the anvil first. Continued rotation of the driving disc 510 causes the first and second driving pins 520 and 522, respectively, to continue to rotate, which, in turn, causes the first slide 526 to translate proximally and away from the pusher 110a (this minimizes a bending load on the anvil), and the second slide 528 to continue to translate distally toward the set of pushers 110b such that the plurality of fasteners 108b deploy from the cartridge 22 and into the anvil pocket(s) on the anvil (FIG. 6C).

In use, prior to actuation of trigger actuator 102, thrust bar 504 is in an initial proximal position (e.g., start position, see FIG. 6A). Actuation of trigger actuator 102 causes thrust bar 504 to translate distally causing the driving disc 510 to rotate in a counter-clockwise direction (see FIG. 6B, for example). As driving disc 510 rotates, first and second drive pins 520 and 522, respectively, cause a respective slide 526 and 528 to translate distally toward the respective set of pushers 110a and 110b. The spacing configuration of the slides 526 and 528 in combination with the positioning of the first and second drive pins 520 and 522, respectively, on the driving disc 510 facilitate in forming the set of surgical fasteners 108a first, and subsequently deploying and forming the set of surgical fasteners 108b next. More particularly, because the first slide 526 is positioned distal the slide 528, first slide 526 contacts the set of pushers 110a prior to the second slide 528 contacting the set of pushers 110b. Thus, the set of fasteners 108a deploy from the cartridge 22 and into the anvil pocket(s) on the anvil first. Continued rotation of the driving disc 510 causes the first and second driving pins 520 and 522, respectively, to continue to rotate, which, in turn, causes the first slide 526 to translate proximally and away from the pusher 110a (this minimizes a bending load on the anvil), and the second slide 528 to continue to translate distally toward the set of pushers 110b such that the plurality of fasteners 108b deploy from the cartridge 22 and into the anvil pocket(s) on the anvil (FIG. 6C).

With reference now to FIGS. 7A-7C, and initially with reference to FIG. 7A, an alternate embodiment of a firing mechanism is shown generally as 600 and described.

A distal end of thrust bar 604 includes a head portion 606 configured to engage at least one pusher 110 to effect ejection of fastener(s) 108 disposed within cartridge 22. In the embodiments illustrated in FIGS. 7A-7C, head 606 includes a distal end 606a that is configured to operatively couple to links 612 (three links 612a, 612b, 612c are shown). With this purpose in mind, distal end 606a includes one or more pivot pins or cam pins 608 that operatively couple to the links 612a, 612b.

Each link 612a, 612b, and 612c is disposed between head 606 and pushers 110. Link 612a includes a proximal end operatively coupled (e.g., by way of pivot pin 608) to a top portion of the distal end 606a of head 606 and a distal end that operatively couples to a bottom portion of link 612c by way of a pivot pin or cam pin 614. Link 612b includes a proximal end operatively coupled to a bottom portion of the distal end 606a of head 606 (e.g., by way of pivot pin 608) and a distal end that operatively couples to a top portion of link 612c by way of a pivot pin 608. Link 612c includes a distal pusher contacting surface 612c₁ that is configured to contact and force one or more pushers 110 distally. Each link 612a, 612c operatively couples and/or mechanically engages a slot 616.

Pivot pin 614 is configured to translate within a slot 616 operatively disposed adjacent a bottom portion of the end effector. Slot 616 may have the same or similar configurations and/or geometries as hereinbefore described slots. Additionally, slot 616 may include structure and/or materials (e.g., a groove and/or lubricant, not explicitly shown) that facilitates movement of pivot pin 614 therein. Slot 616 is located at a predetermined position within the end effector 16. Slot 616 includes proximal and distal ends 616a, 616b, respectively. As with the previously described slots (e.g., slots 414), in embodiments, slot 616 may include a portion that is bent, arcuate or curved adjacent distal end 616b thereof; this bend or arcuate portion provides a path for the link 612c, such that at least a portion of the link 612c (e.g., a bottom portion adjacent pivot pin 614) "overshoots" and causes the surgical fasteners away from a "throat" of the anvil to move. A spring (e.g., spring 116) may be disposed within slot 616 for proximally biasing pivot pin 614. Slot 616 is dimensioned such that pivot pin 614 and/or links 612a, 612c, or portion thereof, is moveable therein from a proximal position to a distal position.

In use, prior to actuation of trigger actuator 102, thrust bar 606 is in an initial proximal position (e.g., start position, see FIG. 7A, for example). Actuation of trigger actuator 102 causes thrust bar 604 to translate distally, which causes the pivot pin 614 and portions of the links 612a, 612b, and 612c to translate distally (links 612a and 612c within the slot 616). This translation causes the bottom most pushers 110n distally (FIG. 7B) to contact its corresponding fasteners 108n prior to pusher 110m contacting its corresponding fastener 108m (FIG. 7B), which, in turn, causes the corresponding fastener(s) 108n, 108m to sequentially deploy from the cartridge 22 and toward anvil 18.

When the pivot pin 614 and links 612a, 612c have translated to a point within the slot 616 where they are prevented from further distally translating (e.g., a distal most end of slot 616), the force exerted on the link 612c by thrust bar 604 causes the link 612c to pivot about the "bottom out point" within the slot 616. As a result, the link 612c is caused to rotate counter clockwise (i.e., in the direction of arrow "H", see FIG. 7B) causing the remaining pushers 110 to be pushed distally, which, in turn, causes the corresponding fasteners 108 to deploy from the cartridge 22 and into anvil pocket(s) on the anvil 18 (FIG. 7C). This results in sequential firing of all the fasteners. As noted above, the bent or arcuate portion of the slot 616 allows the bottom portion of link 612c adjacent pivot pin 614 to "overshoot" to form the surgical fasteners 108 away from the "throat" of the anvil.

With reference now to FIGS. 7D-7E, and initially with reference to FIG. 7D, an alternate embodiment of a camming configuration for use with the firing mechanism 600 is described and designated 600a. So as not to obscure the present disclosure with redundant information, only those features that are unique to the camming configuration of firing mechanism 600 illustrated in FIGS. 7D-7E will be described herein.

Each link 612a, 612b, and 612c is disposed between head 606 and pushers 110. Link 612b includes a proximal end operatively coupled to a bottom portion of the distal end 606a of head 606 (e.g., by way of pivot pin 608) and a distal end that operatively couples to a top portion of link 612c by way of a pivot pin 608a. Link 612a includes a generally elongated slot 622 that extends along a length of the link 612a. More particularly, link 612a includes a slot 622 operably disposed adjacent a bottom portion thereof. Slot 622 is configured to couple to the pivot pin or cam pin 614, such that the pivot pin 614 is movable within the slot 622. In the embodiment illustrated in FIGS. 7D-7E, link 712c is disposed at an angle β' with respect to a Y' axis. Link 712c maintains this angle β' with respect to the Y' axis during translation of the link 712c within the cartridge 22 until the pivot pin 608a bottoms out.

Each of pivot pins 608a and 614 is configured to translate within respective slot 620 and 616, with the pivot pin 614 also configured to translate within the slot 622. Slot 616 is configured as previously described herein. Slot 620 is operatively disposed adjacent a top portion of the end effector. Slot 620 may have the same or similar configurations and/or geometries as hereinbefore described slots. Additionally, slot 620 may include structure and/or materials (e.g., a groove and/or lubricant, not explicitly shown) that facilitates movement of pivot pin 608a therein. Slot 620 is located at a predetermined position within the end effector 16. Slot 620 includes proximal and distal ends 620a, 620b, respectively. As with the previously described slots (e.g., slot 616), in embodiments, slot 620 may include a portion that is bent, arcuate or curved adjacent distal end 620b thereof; this bend or arcuate portion provides a path for the link 612c, such that at least a portion of the link 612c (e.g., a top portion adjacent pivot pin 608a) "overshoots" and causes the surgical fasteners away from a "throat" of the anvil to move.

In use, prior to actuation of trigger actuator 102, thrust bar 604 is in an initial proximal position (e.g., see FIG. 7D, for example). Actuation of trigger actuator 102 causes thrust bar 604 to translate distally, which causes the pivot pin 614 and portions of the links 612a, 612b, and 612c to translate distally (links 612a and 612c within the slot 616, and links 612b and 612c within the slot 620). During translation of the links 612a, 612b, and 612c within the respective slots, link 712c maintains the angle β' with respect to the Y' axis during translation of the link 712c within the cartridge 22 until the pivot pin 608a "bottoms out." This translation causes the top most pushers 110a distally (FIG. 7E) to contact its corresponding fasteners 108a prior to pusher 110b contacting its corresponding fastener 108b (FIG. 7E), which, in turn, causes the corresponding fastener(s) 108m, 108n to sequentially deploy from the cartridge 22 and toward anvil 18.

When the pivot pin 608a and links 612b, 612c have translated to a point within the slot 620 where they are prevented from further distally translating (e.g., a distal most end of slot 620), the force exerted on the link 612c by thrust bar 604 causes the link 612c to pivot about the "bottom out point" within the slot 620. As a result, the link 612b is caused to rotate clockwise (i.e., in the direction of arrow "$H_1$", see FIG. 7E) causing the remaining pushers 110 to be pushed distally, which, in turn, causes the corresponding fasteners 108 to deploy from the cartridge 22 and into anvil pocket(s) on the anvil 18. This results in sequential firing of all the fasteners (FIG. 7F). As noted above, the bent or arcuate portion of the slot 616 allows the bottom portion of link 612c adjacent pivot pin 614 to "overshoot" to form the surgical fasteners 108 away from the "throat" of the anvil.

With reference now to FIGS. 8A-8E, and initially with reference to FIG. 8A, an alternate embodiment of a firing mechanism is shown generally as 700 and described.

A distal end of thrust bar 704 includes a head portion 706 configured to engage at least one pusher to effect ejection of fastener(s) 108 disposed within cartridge 22. In the embodiments illustrated in FIGS. 8A-8C, head 706 includes a distal end 706a that is configured to mechanically engage one or more links 712 (three links 712a, 712b, 712c are shown). With this purpose in mind, distal end 706a may have any suitable shape and may include structure that operatively couples distal end 706a to the one or more of links 712 (e.g., link 712a). For example, a distal end 706a may operatively couple to one or more links 712 by way of a cam slot and cam pin configuration. More particularly, distal end 706a of head portion 706 includes an elongated vertically disposed cam slot 730 that is configured to operably couple to a corresponding cam pin 714 disposed on link 712a.

Each of links 712a, 712b, and 712c is disposed between the head 706 and pushers 110. Link 712a includes a bottom end pivotably connected to the end effector 16 by way of a pivot pin 738 (or the like) and a top end operatively coupled to a top end of link 712b by way of a pivot pin or cam pin 718 that is operatively associated with a slot 716 adjacent the distal end 706 of thrust bar 704. Link 712a includes a proximal end that includes a cam pin 714 that is operably disposed within the cam slot 730 and operably couples the distal end 706a to the link 712a. Link 712b includes a top end that is pivotably coupled to link 712a via pivot pin 718 and a bottom end that pivotably couples to a bottom end of link 712c via a pivot pin or cam pin 734 that is operatively associated with a slot 736. Link 712c includes a bottom end that pivotably connects to the bottom end of link 712b and a top end that pivotably connects to the end effector by way of a pivot pin 732 (or the like). Link 712c includes a distal pusher contacting surface $712c_1$ that is configured to contact and force forward one or more pushers 110.

Pivot pins 718, 734 are configured to translate within the slots 716 and 736, respectively, and are operatively disposed adjacent a top portion and bottom portion, respectively, of the end effector. Slots 716 and 736 may have the same or similar configurations and/or geometries as hereinbefore described slots. Additionally, slots 716 and 736 may include structure and/or material (e.g., a groove and or lubricant, not explicitly shown) that facilitates movement of links 712a, 712b, and 712c therein (e.g., a groove, not explicitly shown). Slots 716 and 736 are located at a predetermined position within the end effector 16. Slot 716 includes respective proximal and distal ends 716a, 716b. Likewise, slot 736 includes respective proximal and distal ends 736a, 736b. As with previously described slots (e.g., slot 720), slots 716, 736 include a portion that is arcuate or curved near or at a distal end thereof. More particularly, the curved distal ends of each of the slots 716, 736 extend inwardly and toward one another. The slots 716, 736 include radiuses of curvature that are equal to each other. A spring (e.g., 116) may be disposed within slots 716, 736 and coupled to pivot pins 718, 734 and/or links 712a, 712b, or portions thereof. Slots 716, 736 are dimensioned such that the respective pivot pins 718, 734 and/or links 712a, 712b, or portions thereof, is moveable therein from a proximal position to a distal position.

In use, prior to actuation of trigger actuator 102, thrust bar 706 is in an initial proximal position (e.g., start position, see FIG. 8A, for example). Actuation of trigger actuator 102 causes thrust bar 704 to translate distally. As head 706 translates distally, the configuration of links 712 in combination with the cam pins 718 and 734 force the link 712a to translate distally within the slots 716, 736 and link 712b to pivot counter clockwise (i.e., in the direction of arrow "I") which causes link 712c to pivot and rotate clockwise (i.e., in the direction of arrow "J"). This rotation of links 712b, 712c causes distal translation of the top most pusher 110a to contact its corresponding fastener 108a prior to pusher 110b contacting its corresponding fasteners 108b (FIG. 8B), which, in turn, causes the corresponding fastener(s) 108a, 108b to sequentially deploy from the cartridge 22 and toward the anvil 18. As can be appreciated, the link 712c sequentially contacts the remaining pushers 110, each of which sequentially contacts its corresponding fastener 108. This results in sequential firing of all the fasteners 110 (FIG. 8C).

In certain embodiments, the distal end 706a of head 706 may operably couple to the link 712a via one or more other suitable configurations. For example, a firing mechanism 700a may include a distal end $706a_{-1}$ having a generally "L" shape, see FIG. 8D, for example (or "T" shape, not explicitly shown). Alternatively, a firing mechanism 700b may include a distal end $706a_{-2}$ having a generally rounded shape (FIG. 8E). In each of the embodiments illustrated in FIGS. 8D and 8E, each of the respective distal ends $706a_{-1}$ and $706a_{-2}$ is configured to contact the link 712a during distal translation of the thrust bar 704. The operational and functional features of each the firing mechanism 700a and 700b depicted in FIGS. 8D and 8E, respectively, is identical to that of the firing mechanism 700 depicted in FIGS. 8A-8C and, as a result thereof, will not be described in detail any further.

With reference now to FIGS. 9A-9G, and initially with reference to FIG. 9A, an embodiment of a firing mechanism is shown generally as 800 and described.

A distal end of thrust bar 804 includes a head portion 806 configured to engage at least one pusher 110 to effect ejection of fasteners 108 disposed within cartridge 22. Head portion 806 is in mechanical communication with one or more a wedges or cams 812 (cam 812). In the embodiments illustrated in FIGS. 9A-9F, a distal end 806a of the head portion 806 functions as a rack in the rack and pinion configuration and includes a plurality of teeth 828 (see FIG. 9B, for example) configured to mesh or engage with a corresponding plurality of teeth 826 of a gear wheel 824 associated with the cam 812, to be described in greater detail below. In certain embodiments, an internally disposed groove or channel (not shown) may be operatively disposed along a length of the cartridge 22. The channel may be configured to receive a portion of the thrust bar 804 and/or head portion 806, or portion(s) thereof (e.g., a distal end 806a of the). To this end, the channel may be proportionately dimensioned to accommodate translation of the thrust bar 804 and/or head portion 806.

Camming member or cam 812 is disposed between the head 806 and pusher(s) 110. The geometry of cam 812 is configured such that cam 812, or portions thereof, is introduced to the pusher(s) 110 in a sequential or consecutive manner. The cam has a helical configuration and a plurality of teeth. When rotated, the teeth are advanced with respect to the pushers in a sequential or consecutive manner. To this end, cam 812 is pivotably and/or rotatably mounted within the end effector adjacent the plurality of pusher(s) and proximal relative thereto. More particularly, cam 812 extends substantially parallel along a Y" axis (FIG. 9A). Cam 812 extends or spans at least a length of the pusher(s) 110 and/or fastener(s) 108. In embodiments, cam 812 includes a plurality of spaced apart teeth 820 that extend along the length of cam 812 at predetermined locations thereof (see FIGS. 9A-9C, for example). Alternatively, a cam 812a may include a continuous structure having a twisted configuration (see FIGS. 9D-9F, for example). In embodiments, a cam 812 may be biased proximally by way of one or more springs or the like (not shown).

In the embodiments illustrated in FIGS. 9A-9F, cam 812 includes an axle 822 that extends longitudinally through the camming member or cam 812. More particularly, a top portion of the axle 822 operatively couples to a frame of the cartridge 22 and a bottom portion of the axle 822 couples to a gear wheel 824 that operably couples to the frame of the cartridge 22. The gear wheel 824 functions as a pinion in a rack and pinion configuration and includes a plurality of teeth 826 (FIG. 9B) configured to mesh or engage the plurality teeth 828 associated with the distal end 806a. Depending on design constraints associated with the end effector 16, the axle 822 and cam 812 may rotate together, or the cam 812 may rotate with respect to the axle 822.

In further embodiments, the camming member or cam 812 can be rotated by a cable attached to axle 822. Furthermore, the cam 812 can be rotated by a rotating shaft that actuates one or more gears enmeshed with the gear wheel 824. The cam 812 can be rotated utilizing other driver members, such as thrust bars, cables, gears, rotating shafts, etc.

Operation of the firing mechanism 800 is described in terms of use with embodiment illustrated in FIGS. 9D-9E. In use, prior to actuation of trigger actuator 102, thrust bar 804 is in an initial proximal position (see FIG. 9D, for example). Actuation of trigger actuator 102 causes thrust bar 804 to translate distally, which causes the plurality of teeth 828 of the distal end 806a to mesh or engage the plurality of teeth 826 on the gear wheel 824. Rotation of the gear wheel 824 causes the cam 812 to rotate about the Y" axis in a clockwise direction towards pusher(s) 110, causing the pusher(s) 110 (e.g., bottom most pusher 110n) distally to contact its corresponding fastener(s) (e.g., bottom most fastener 108n) prior to pusher 110m contacting its corresponding fastener 108m, which, in turn, causes the corresponding fastener(s) 108n, 108m to sequentially deploy from the cartridge 22 and toward the anvil. As can be appreciated, the cam 812 sequentially contacts the remaining pushers 110, each of which sequentially contacts its corresponding fastener 108 (see FIGS. 9E and 9F, for example). Additionally, it is contemplated and within the scope of the present disclosure that each tooth 820 of camming member or cam 812 directly contacts a fastener 110. Additionally, it is envisioned that each tooth 820 or each pusher 110 contacts more than one fastener 110 (see FIG. 9B, for example).

As shown in FIG. 9D, the camming member or cam 812 can have a helical configuration with an edge that sequentially contacts pushers as the cam is rotated, in contrast to the plurality of teeth shown in FIG. 9A, for example.

FIG. 9G illustrates alternative methods and/or structures for rotating the cam 812.

More particularly, in the embodiment illustrated in FIG. 9G camming member or cam 812 includes a generally cylindrical bottom portion 812c and an axle 830 that extends longitudinally through the cam 812. A top portion of the axle 830 operatively couples to a frame of the cartridge 22 and a bottom portion of the axle 830 couples to the frame of the cartridge 22 (as described hereinbefore with respect to FIGS. 9A-9F)). A separate gear wheel 832 functions as a pinion in a rack and pinion configuration and includes a plurality of teeth 834. The gear wheel 832 is operatively disposed adjacent to the cam 812. The gear wheel 832 operably couples (via an axle or pin 836) to the frame of the cartridge 22. A generally cylindrical member 838 extends from a top surface of the gear wheel 832 and includes a diameter of suitable proportion, such that a pulley 840 may be tautly wrapped therearound. More particularly, a pulley 840 provides mechanical communication between the cam 812 and the cylindrical member 838. In the embodiment illustrated in FIG. 9G, a distal end 806a of the head portion 806 functions as a rack in the rack and pinion configuration and includes a corresponding plurality of teeth 828 configured to mesh or engage with the plurality of the teeth 834 of the gear wheel 832, as described above with respect to FIGS. 9D-9F. In the embodiment illustrated in FIG. 9G, distal movement of the distal end 906a causes the gear wheel 832 to rotate in a clockwise direction, which, in turn, causes the cylindrical member 838 and, thus, the pulley 840 to also rotate in the clockwise direction. Clockwise rotation of the pulley 840 causes the cam 812 to rotate, which, in turn, causes the pusher(s) 110 and corresponding fastener(s) 108 to deploy in a manner as described hereinbefore with respect to FIGS. 9D-9F.

Figure 10A:
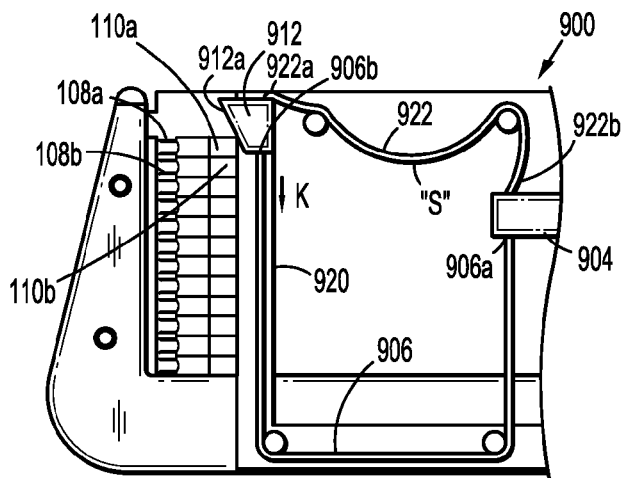
Figure 10B:
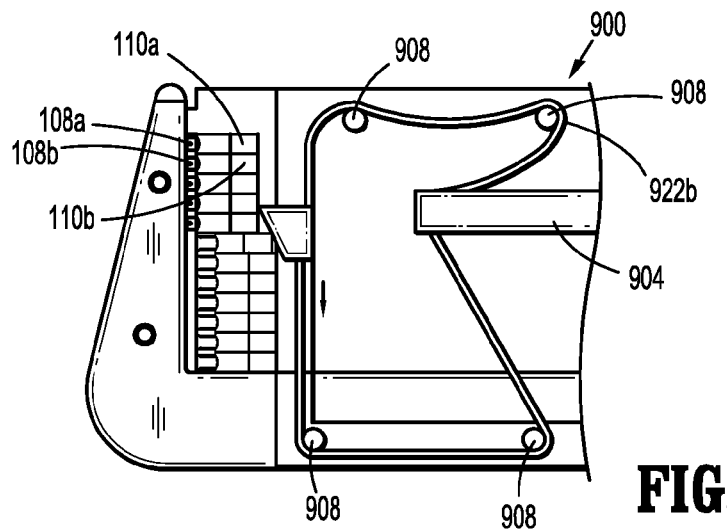
Figure 10C:
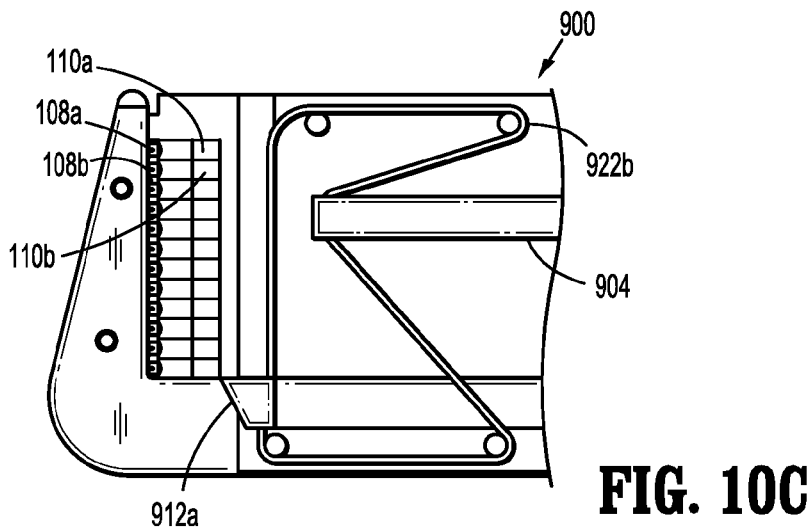

With reference now to FIGS. 10A-10C, and initially with reference to FIG. 10A, an alternate embodiment of a firing mechanism is shown generally as 900 and described.

A distal end 904a of a thrust bar 904 operatively couples (e.g., rivet or pin not explicitly shown) to a bendable member 906 configured to engage at least one pusher 110 to effect ejection of fasteners 108 disposed within cartridge 22. In the embodiments illustrated in FIGS. 10A-10C, bendable member 906 includes a distal end 906b that operatively couples to a wedge or cam 912 and a proximal end 906a that operatively couples to or is formed with the distal end 904a of thrust 904. Bendable member 906 may be configured from any suitable material known in the art including but not limited to metals, plastics, etc. In embodiments, bendable member 906 is formed of a thin sheet of metal or metal alloy or wire. Bendable member 906 may ride along or within a track or channel 920 that extends within the end effector (see FIG. 10A, for example). A bendable member 922 (similar to that of bendable member 906) includes a distal end 922a that operatively couples to a top portion of the wedge or cam 912 and a proximal end 922b that operatively couples to or is formed with the distal end 904a of thrust 904. Bendable member 922 includes a degree of slack "S" defined by a length that is approximately equal to the distance that the thrust bar 904 translates. In this instance, after the thrust bar 904 has translated a distance that is equal to the length of the slack "S", the bendable member 904 becomes taut between the distal end 922a coupled to the top portion of the cam 912 and the proximal end 922b coupled to the distal end 904a of the pusher facilitating resetting the cam 912 to an initial position.

One or more pulleys 908 (four pulleys are shown) are operatively disposed at predetermined locations within end effector 16. Alternatively, rivets or non-rotating features may used in place of the pulleys. In embodiments illustrated in FIGS. 10A-10C, a pair of bottom pulleys 908 are configured such that as thrust bar 904 is translated distally the cam 912 is caused to translate in a downward direction, and a pair of top pulleys 908 are configured such that as thrust bar 904 is translated proximally the cam 912 is caused to translate in an upward direction, that is, the cam 912 is reset to an initial position. Alternatively, a pulley 908 is configured such that as thrust bar 904 is translated distally, the cam 912 is caused to translate in an upward direction (see FIGS. 10D-10F, for example).

In the embodiments illustrated in FIGS. 10A-10C, cam 912 includes a distal portion 912a that is disposed at an angle with respect to proximal portion of pushers 110. A top portion 912b of cam 912 operably couples to the distal end 922a of the bendable member 922a and a bottom portion 912c operably couples to the distal end 906b of the bendable member 906a by any suitable means.

In use, prior to actuation of trigger actuator 102, thrust bar 904 is in an initial proximal position (e.g., start position, see FIG. 10A, for example). Actuation of trigger actuator 102 causes thrust bar 904 to translate distally. The pulley configuration forces the cam 912 to translate downward (as shown by the arrow "K") within the end effector and along side the pusher(s) 110. The shape of cam 912 causes the top most pusher 110a distally to contact its corresponding fastener 108a prior to pusher 110b contacting its corresponding fastener 108b (FIG. 10B), which, in turn, causes the corresponding fastener(s) 108a, 108b to sequentially deploy from the cartridge 22 and toward the anvil 18. As can be appreciated, the cam 912 sequentially contacts the remaining pushers 110, each of which sequentially contacts its corresponding fastener 108. This results in sequential firing of all the fasteners 108 (see FIG. 10C, for example). After all the fasteners have been fired, the thrust bar 904 is in a distal most position and the slack "S" originally associated with the bendable member 922 is not present and the bendable member 922 is pulled taut (FIG. 10C). Proximal translation of the thrust bar 904 pulls the bendable member 922 which, in turn, facilitates the cam 912 in returning to the initial position (FIG. 10A). As can be appreciated by one of skill in the art, the firing mechanism 800 may be configured to function without the need for the top pulley configuration.

Figure 10D:
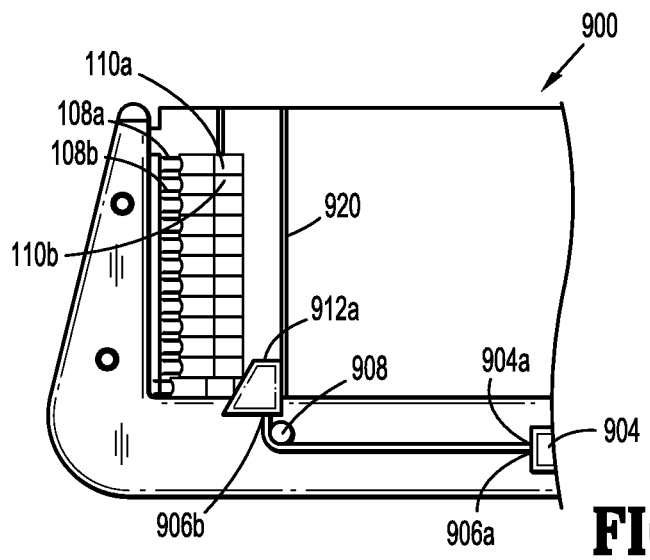
Figure 10E:
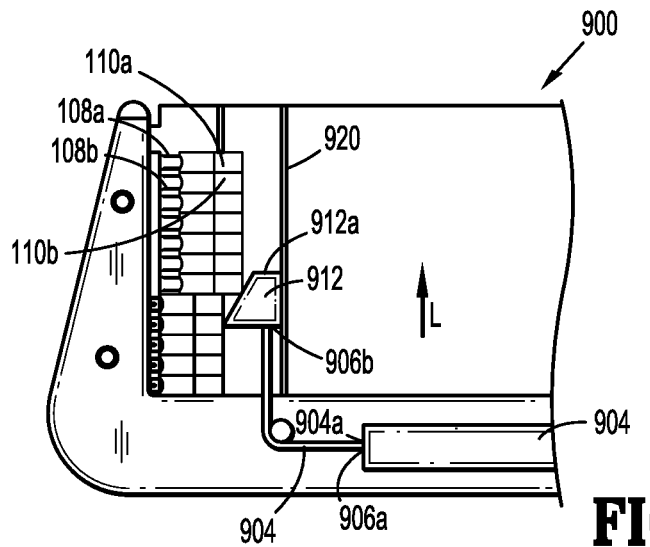
Figure 10F:
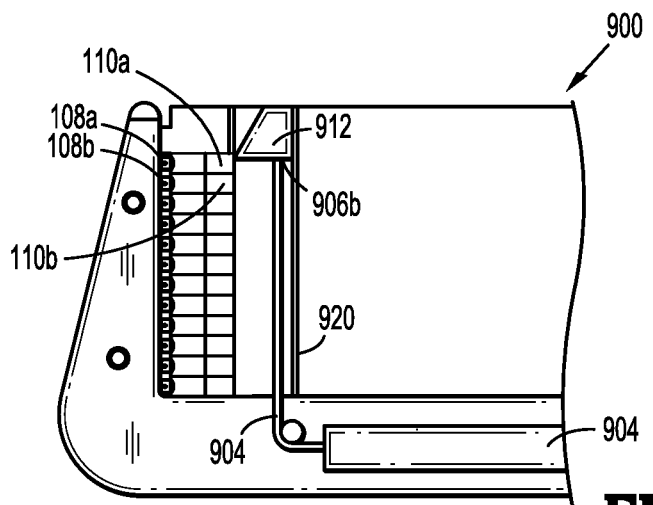

With reference now to FIGS. 10D-10F, and initially with reference to FIG. 10D, an alternate embodiment of camming configuration for use with a firing mechanism 900 is described.

Thrust bar 904 is operably disposed adjacent a bottom portion of the end effector 16. A distal end 904a of a thrust bar 904 operatively couples (e.g., rivet or pin not explicitly shown) to a bendable member 906 configured to engage at least one pusher 110 to effect ejection of fasteners 108 disposed within cartridge 22. In the embodiments illustrated in FIGS. 10D-10F, bendable member 906 includes a distal end 906a that operatively couples to a wedge or cam 912 and a proximal end 906a that operatively couples to or is formed with the distal end 904a of thrust bar 904. Bendable member 906 may be configured from any suitable material known in the art including but not limited to metals, plastics, etc. In embodiments, bendable member 906 is formed of a thin sheet of metal or metal alloy or wire. Bendable member 906 may ride along or within a track or channel 920 that extends within the end effector.

One or more pulleys 908 (one pulley is shown) is operatively disposed at a predetermined location within end effector 16. Alternatively, rivets or non-rotating features may used in place of the pulleys. In embodiments illustrated in FIGS. 10D-10F, a bottom pulley 908 is configured such that as thrust bar 904 is translated distally the cam 912 is caused to translate in an upward direction.

In the embodiments illustrated in FIGS. 10D-10F, cam 912 includes a distal portion 912a that is disposed at an angle with respect to proximal portion of pushers 110. A bottom portion 912a of cam 912 operably couples to a distal end 906a of bendable member 906 by any suitable means.

In use, prior to actuation of trigger actuator 102, thrust bar 904 is in an initial proximal position (see FIG. 10D, for example). Actuation of trigger actuator 102 causes thrust bar 904 to translate distally, which causes bar 904 to translate distally. The pulley configuration forces the cam 912 to translate upward (as shown by the arrow "L") within the end effector and along side the pusher(s) 110. The shape of cam 912 forces the bottom most pusher 110n distally to contact its corresponding fastener 108n prior to pusher 110m contacting its corresponding fastener 108m (FIG. 10E), which, in turn, causes the corresponding fastener(s) 108n, 108m to sequentially deploy from the cartridge 22 and toward the anvil 18. As can be appreciated, the cam 912 sequentially contacts the remaining pushers 110, each of which sequentially contacts its corresponding fastener 108. This results in sequential firing of all the fasteners 108 (see FIG. 10F, for example).

Figure 10G:
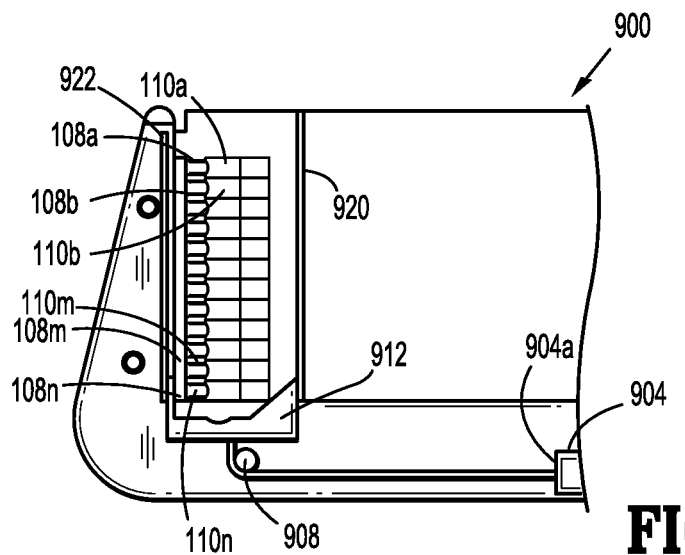
Figure 10H:
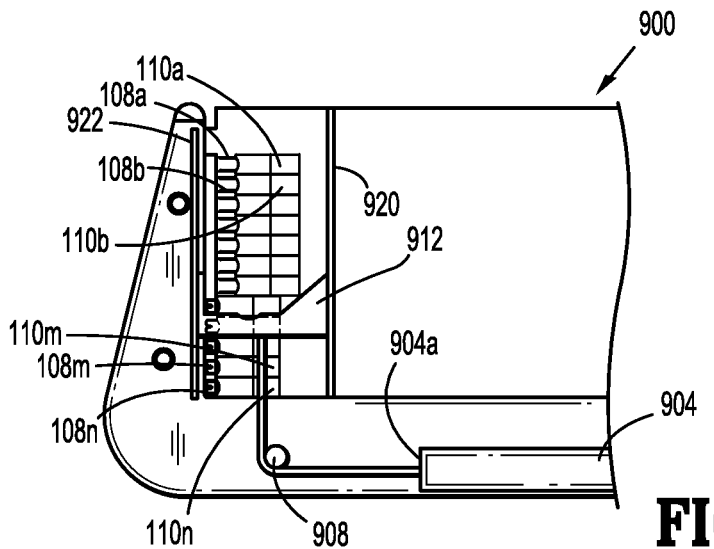
Figure 10I:
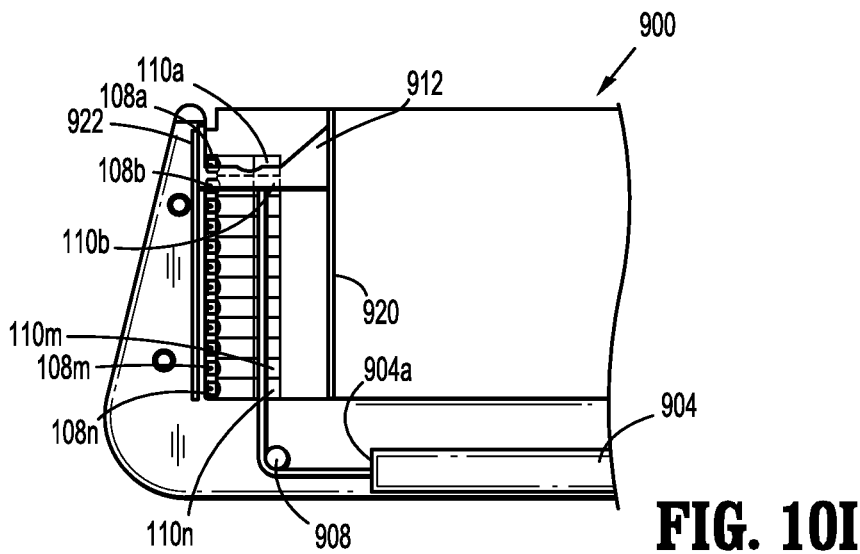

In an embodiment illustrated in FIGS. 10G-10I, cam 912 is configured to translate within tracks 920 that are disposed at predetermined locations in both the cartridge 22 and anvil 18. In use, as the bendable portion is translated distally, the cam 912 translates upward (or some instances downward) causing the pushers 110 and corresponding fasteners 108 to deploy as described above. A knife or cutter (not explicitly shown) may be incorporated into the cam 912 and configured to cut or sever tissue after deployment of the pushers 110 and corresponding fasteners 108. In the embodiment described in FIGS. 10G-10I, it is envisioned that cam 912 helps maintain alignment and spacing between the cartridge 22 and anvil 18 during deployment of the fasteners 108 to help improve fastener formation.

With reference now to FIGS. 11A-11C, and initially with reference to FIG. 11A, an alternate embodiment of a firing mechanism is shown generally as 1000 and described.

A distal end of thrust bar 1004 includes a head portion 1006 configured to engage at least one pusher to effect ejection of fasteners 108 disposed within cartridge 22. In the embodiments illustrated in FIGS. 11A-11C, head 1006 includes a distal end 1006a that is configured to mechanically engage one or more independently moveable cams 1012 (three cams 1014, 1016, 1018 are shown). With this purpose in mind, distal end 1006a of head 1006 may have any suitable shape and may include structure that operatively couples distal end 1006a to one or more of cams 1012. More particularly, head 1006 includes a generally flat distal end 1006a configured to contact a bottom cam 1018. Distal end 1006a is operably disposed adjacent a bottom portion of the end effector 16.

Each of the cams 1012 is disposed between the head 1006 and pushers 110. In the embodiments illustrated in FIGS. 11A-11C, cams 1012 are configured to cause sequential distal translation of the pushers 110. With this purpose in mind, the cams 1012 are positioned one on top of the other and in a staggered configuration (see FIG. 11A for example). More particularly, cam 1014 includes substantially flat top surface 1014a that is disposed adjacent a top portion of the end effect 16 and a stepped bottom surface 1014b that is adjacent and corresponds to stepped top surface 1016a of the cam 1016 (FIGS. 11A-11C). Stepped bottom surface 1014b includes three steps. The proximal most step being proportioned to form part of a housing for a resilient member 1020. Cam 1014 includes one or more slots 1014c configured to ensure linear translation of the cam 1014 when the cam 1014 is forced distally. To this end, slot 1014c is configured to support or house a cam pin 1014d (FIG. 11B) moveable therein between a proximal position to a distal position. A cam 1016 includes stepped top and bottom surfaces 1016a and 1016b, respectively, that are disposed adjacent stepped bottom surface 1014b of cam 1014 and a stepped top surface 1018a of the cam 1018, respectively (FIGS. 11A-11C). Stepped top and bottom surfaces 1016a and 1016b, respectively, include three steps. A middle step of the stepped top surface 1016a being proportioned to form part of the housing for a resilient member 1020 and a proximal step of the stepped bottom surface 1016b being proportioned to form part of a housing for a resilient member 1020. Cam 1016 includes one or more slots 1016c configured to ensure linear translation of the cam 1016 when the cam 1016 is forced distally. To this end, slot 1016c is configured to support or house a cam pin 1016d (FIG. 11B) moveable therein between a proximal position to a distal position. A cam 1018 includes substantially flat bottom surface 1018b that is disposed adjacent a bottom portion of the end effect 16 and a stepped top surface 1018b that corresponds to stepped bottom surface 1016b of the cam 1016 (FIGS. 11A-11C). Stepped top surface 1018b includes three steps. A middle step being proportioned to form part of a housing for a resilient member 1020. Cam 1018 includes one or more slots 1018c configured to ensure linear translation of the cam 1018 when the cam 1018 is forced distally. To this end, slot 1018c is configured to support or house a cam pin 1018d (FIG. 11B) moveable therein between a proximal position to a distal position. The stepped configuration associated with each of the cams 1012 provides a smooth, linear transition when the cams 1012 are forced distally. Each of the cams 1014, 1016, 1018 includes a respective distal surface 1014e, 1016e, 1018e dimensioned to contact one or more pushers 110, and the cam 1018 includes a proximal surface 1018f dimensioned to contact head 1006. Distal surface 1014e of cam 1014 is initially disposed distally relative to distal surface 1016e of cam 1016 and distal surface 1018e. And, distal surface 1016e of cam 1016 is initially disposed distally relative to distal surface 1018e of cam 1018. Accordingly, the distal surface of cam 1014 contacts a corresponding set of pusher(s) first, the distal surface of cam 1016 contacts a corresponding set of pusher(s) next, and so on.

One or more resilient members or springs 1020 is disposed between the cam 1014 and 1016, and one or more springs 1020 is disposed between the cams 1016 and 1018 (see FIGS.

11A-11C). More particularly, a spring 1020 is disposed between the proximal most step of cam 1014 and the middle step of the stepped top surface of cam 1016, and a spring 1020 is disposed between the proximal most step of the stepped bottom surface of the cam 1014 and the middle step of cam 1018. The springs 1020 are configured to bias the cams 1016 and 1018 proximally and, thus help ensure that distal surfaces of the cams 1012 contact a corresponding set of the pusher(s) 110 sequentially.

In use, prior to actuation of trigger actuator 102, thrust bar 1004 is in an initial proximal position (FIG. 11A, for example). Actuation of trigger actuator 102 causes thrust bar 1004 to translate distally, which causes head 1006 to contact the proximal surface of the cam 1018. The configuration of cams 1012 (i.e., the staggered configuration of the distal surfaces of each of the cams 1012) in combination with the biasing force of the springs 1020 provides that each of the cams 1012 translate distally together. The springs 1020 include appropriate spring constants such that the distal surfaces 1016e and 1018e of the cams 1016 and 1018, respectively, do not contact a corresponding pusher(s) until the distal surface 1014e of the cam 1014 contacts its pusher(s) and bottoms out (FIG. 11B). Accordingly, cam 1014 causes the top most pusher(s) 110a distally to contact its corresponding fastener(s) 108a prior to pusher 110b contacting its corresponding fastener(s) 108b (FIG. 11B), which, in turn, causes the corresponding fastener(s) 108a 108b to sequentially deploy from the cartridge 22 and toward the anvil 18.

When cam 1014 has translated to a point where it is prevented from further translating, the force exerted on cam 1016 by thrust bar 1004 overcomes the force exerted on the cam 1016 by the he spring 1020, which causes the cam 1016 to translate distally. This process continues for each of the remaining cams, e.g., cam 1018 and so forth, causing the remaining pushers(s) 110 be pushed distally, which, in turn, causes the corresponding fastener(s) 108 to deploy from the cartridge 22 and into anvil pocket(s) on the anvil (FIG. 11C). As can be appreciated, each of the remaining cams 1012 (e.g., 1018 and so forth) independently and sequentially contacts the remaining pushers 110, each of which sequentially contacts its corresponding fastener(s) 108. This results in sequential firing of all the fasteners 110.

With reference now to FIGS. 11D-11F, an alternate embodiment of a camming configuration for use with a firing mechanism 900a is described.

A distal end of thrust bar 1004 includes a head portion 1006 configured to engage at least one pusher to effect ejection of fasteners 108 disposed within cartridge 22. In the embodiments illustrated in FIG. 11D, head 1006 includes a distal end 1006a that is configured to mechanically engage one or more independently moveable cams 1040 (three cams 1042, 1044, 1046 are shown). With this purpose in mind, distal end 1006a of head 1006 may have any suitable shape and may include structure that operatively couples distal end 1006a to one or more of cams 1040. More particularly, head 1006 includes a generally flat distal end 1006a configured to contact a middle cam 1044. Distal end 1006a is operably disposed adjacent a middle portion of the end effector 16.

Each of the cams 1040 is disposed between the head 1006 and pushers 110. In the embodiments illustrated in FIG. 11D, cams 1040 are configured to cause sequential distal translation of the pushers 110. With this purpose in mind, the cams 1040 are positioned one on top of the other and in a generally staggered configuration (see FIG. 11D for example). More particularly, a pair of top and bottom cams 1042 and 1046 include respective substantially flat top and bottom surfaces 1042a, 1046a that are disposed adjacent respective top and bottom portions of the end effect 16. A bottom surface 1042b of the cam 1042 includes a protrusion or nib 1042c operably disposed at a predetermined position along the surface 1042b. Likewise, a top surface 1046b of the cam 1046 includes a protrusion or nib 1046c operably disposed at a predetermined position along the surface 1046b. Each of the cams 1042 and 1046 includes a respective distal surface 1042e and 1046e configured to contact one or more corresponding pusher(s) 110. A cam 1044 is in mechanical communication with each of the cams 1042 and 1044 and is operably disposed therebetween. More particularly, cam 1044 includes a generally "dumbbell" like configuration having a proximal surface 1044d configured to contact a distal end 1006a of the head 1006 and a distal surface 1044e configured to contact one or more corresponding pusher(s) 110. A top portion of the cam 1044 includes a gap 1044f that separates the proximal surface 1044d and distal surface 1044e. Similarly, a bottom portion of the cam 1044 includes a gap 1044g that separates the proximal surface 1044d and distal surface 1044e. Each of the gaps 1044f and 1044g is configured to accommodate a respective nib 1042c and 1046c and a resilient member 1020.

One or more resilient members or springs 1020 is disposed between the cam 1042 and 1044, and one or more springs 1020 is disposed between the cams 1044 and 1046 (see FIG. 11D). More particularly, a spring 1020 is disposed between the nib 1042c of cam 1042 and a proximal surface 1044d of the cam 1044, and a spring 1020 is disposed between the nib 1046c of cam 1046 and a proximal surface 1044d of the cam 1044. The springs 1020 are configured to bias the cam 1044 proximally and, thus help ensure that distal surfaces of the cams 1012 contact a corresponding set of the pusher(s) 110 sequentially.

In use, prior to actuation of trigger actuator 102, thrust bar 1004 is in an initial proximal position (FIG. 11D, for example). Actuation of trigger actuator 102 causes thrust bar 1004 to translate distally, which causes head 1006 to contact the proximal surface 1044d of the cam 1044. The structural configuration of cams 1040 (i.e., the nibs 1042c and 1046c in combination with the biasing force of the springs 1020) provides that each of the cams 1012 translate distally together. The springs 1020 include appropriate spring constants such that the distal surface 1044e of the cam 1044 contacts a corresponding pusher(s) until each of the distal surfaces 1042e and 1046e of the cams 1042 and 1046, respectively, contacts its pusher(s) and bottoms out. Accordingly, cams 1042 and 1046 cause the top and bottom most pusher(s) 110a and 110n, respectively, distally to contact its corresponding fastener(s) 108a and 108n, respectively, prior to pusher 110b contacting its corresponding fastener(s) 108b, which, in turn, causes the corresponding fastener(s) 108a and 108n, and 108b to sequentially deploy from the cartridge 22 and toward the anvil 18 (FIG. 11E).

When each of the cams 1042 and 1046 have translated to a point where it is prevented from further translating, the force exerted on cam 1044 by thrust bar 1004 overcomes the force exerted on the cam 1044 by the springs 1020, which causes the cam 1044 to translate distally causing the remaining pushers(s) 110 be pushed distally, which, in turn, causes the corresponding fastener(s) 108 to deploy from the cartridge 22 and into anvil pocket(s) on the anvil. This results in sequential firing of all the fasteners 110 (FIG. 11F).

With reference now to FIGS. 12A-12C, and initially with reference to FIG. 12A, an alternate embodiment of a firing mechanism is shown generally as 1100 and described.

A distal end of thrust bar 1104 includes a head portion 1106 configured to engage at least one pusher 110 to effect ejection of fasteners 108 disposed within cartridge 22. In the embodiments illustrated in FIGS. 12A-12C, head 1106 includes a generally curved end 1106a that is configured to contact at least a portion of a wedge or cam 1112 (cam 112). A cam or pivot pin 1114 is operably disposed at the curved end 1106a.

Cam 1112 is disposed between the head 1106 and pusher 110. In the embodiments illustrated in FIGS. 12A-12C, cam 1112 includes a distal end 1112a and a proximal end 1112b. Distal end 1112a includes a generally flat configuration. The distal end 1112a is configured to contact one or more pushers 110. Proximal end 1112b includes a proximal portion 1112c having an elongated cam slot 1116. Cam 1112 is pivotably connected to the distal end 1106a of head portion 1106 via the cam slot 1116 and pivot pin 1114. A top end of the cam 1112 is pivotably coupled to a top portion of the end effector 16. More particularly, a pivot pin 1118 operably couples the cam 1112 to a frame of the cartridge 22. To ensure that all of the pushers 110 and corresponding surgical fasteners 108 are ejected or deployed, the pivot pin 1118 is operably disposed in-line with a distal most position of the pushers 110 (FIG. 12A). Alternatively, the pivot pin 1118 may be operably coupled to a top portion of the end effector 16.

Slot 1116 may include structure and/or material (e.g., a groove and/or lubricant, not explicitly shown) that facilitates movement of pivot pin 1114 therein.

In use, prior to actuation of trigger actuator 102, thrust bar 1104 is in an initial proximal position (FIG. 12A). Actuation of trigger actuator 102 causes thrust bar 1104 to translate distally, the shape of cam 1112 in combination with the pivot pin 1114 force the cam 1112 to pivot and rotate clockwise (as shown by arrow "M" in FIG. 12B). This rotation of cam 1112 causes distal translation of the top most pusher 110a such that pusher 110a contacts its corresponding fastener 108a prior to pusher 110b contacting its corresponding fastener 108b (FIG. 12B), which, in turn, causes the corresponding fastener(s) 108a, 108b to sequentially deploy from the cartridge 22 and toward the anvil 18. As can be appreciated, the cam 1112 sequentially contacts the remaining pushers 110, each of which sequentially contacts its corresponding fastener 108. This results in sequential firing of all the fasteners 108.

With reference now to FIGS. 13A-13C, and initially with reference to FIG. 13A, an alternate embodiment of a firing mechanism is shown generally as 1200 and described.

A distal end of thrust bar 1204 includes a head portion 1206 configured to engage at least one pusher 110 to effect ejection of fasteners 108 disposed within cartridge 22. In the embodiments illustrated in FIGS. 13A-13C, head 1206 may include a generally curved end (not shown) that is configured to contact at least a portion of a wedge or cam 1212 (cam 112). A cam or pivot pin 1214 is operably disposed at the distal end 1206a.

Cam 1212 is disposed between the head 1206 and pusher 110. In the embodiments illustrated in FIGS. 13A-13C, cam 1212 includes a distal end 1212a and a proximal end 1212b. Distal end 1212a includes a generally flat configuration. The distal end 1212a is configured to contact one or more pushers 110. Proximal end 1212b includes an elongated cam slot 1216. Cam 1212 is pivotably connected to the distal end 1106a of head portion 1206 via the cam slot 1216 and pivot pin 1214. A top and bottom edge 1220 and 1222, respectively, of the proximal end 1212b of the cam 1212 is grounded or secured to a top portion of the end effector 16 via a respective cable 1218 or the like.

Slot 1216 may include structure and/or material (e.g., a groove and/or lubricant, not explicitly shown) that facilitates movement of pivot pin 1114 therein.

In use, prior to actuation of trigger actuator 102, thrust bar 1204 is in an initial proximal position (FIG. 13A). Actuation of trigger actuator 102 causes thrust bar 1204 to translate distally, the shape of cam 1212 in combination with the pivot pin 1214 force the cam 1212 to pivot and rotate clockwise (as shown by arrow "N" in FIG. 13B). This rotation of cam 1212 causes distal translation of the top most pusher 110a such that pusher 110a contacts its corresponding fastener 108a prior to pusher 110b contacting its corresponding fastener 108b (FIG. 13B), which, in turn, causes the corresponding fastener(s) 108a, 108b to sequentially deploy from the cartridge 22 and toward the anvil 18. As can be appreciated, the cam 1212 sequentially contacts the remaining pushers 110, each of which sequentially contacts its corresponding fastener 108. This results in sequential firing of all the fasteners 108.

The present disclosure also relates to methods of using a surgical instrument to sequentially fire fasteners therefrom.

Furthermore, the arrangements shown herein can be utilized in surgical instruments that includes a knife, or an instrument that does not have a knife.

It will be understood that various modifications may be made to the embodiments of the presently disclosed surgical stapling instruments. For instance, an embodiment of the presently disclosed surgical fastening apparatus includes an end effector assembly that includes two cartridge assemblies. An embodiment of the presently disclosed surgical fastening apparatus includes an end effector that is curved. Additionally, it is envisioned that the firing mechanisms of the present disclosure can be used with surgical staplers used for performing anastomoses. Therefore, there above description should not be construed as limiting, but merely as exemplifications of embodiments. Those skilled in the art will envision other modifications within the scope and spirit of the present disclosure.

What is claimed is:

1. A surgical fastening instrument comprising:
a handle portion;
an elongate portion extending distally from the handle portion and defining a longitudinal axis along a length thereof;
an end effector assembly including an anvil and a cartridge supported adjacent a distal end of the elongate portion, each of the anvil and the cartridge including a tissue contacting surface oriented substantially perpendicular to the longitudinal axis;
a plurality of surgical fasteners;
a plurality of pushers;
at least two of the plurality of pushers being independently movable and supporting at least two of the plurality of surgical fasteners;
a driver member coupled to the elongate portion and movable to effect sequential ejection of the at least two surgical fasteners of the plurality of the surgical fasteners from the cartridge;
the plurality of surgical fasteners being in operative communication with the plurality of pushers; and
a camming member rotatably supported between the driver member and the plurality of pushers and being rotatable by the driver member, the camming member having a helical configuration and at least one edge so that when the camming member is rotated by the driver member, the edge contacts the pushers in a consecutive manner.

2. The surgical fastener instrument of claim 1, wherein the driver member is selected from the group consisting of a thrust bar, a cable, and a rotating shaft.

3. The surgical fastener instrument of claim 1, wherein the camming member has a plurality of teeth, and wherein when the camming member is rotated, the teeth are advanced with respect to the pushers in a consecutive manner.

4. The surgical fastener instrument of claim 1, wherein the plurality of surgical fasteners are arranged in linear rows.

* * * * *